US011352443B2

(12) United States Patent
Hammerberg et al.

(10) Patent No.: US 11,352,443 B2
(45) Date of Patent: Jun. 7, 2022

(54) TREATMENT OF ALLERGIC DISEASES WITH CHIMERIC PROTEIN

(71) Applicant: North Carolina State University, Raleigh, NC (US)

(72) Inventors: Bruce Hammerberg, Raleigh, NC (US); Sitka Eguiluz-Hernandez, Raleigh, NC (US); Thierry Olivry, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 192 days.

(21) Appl. No.: 15/934,834

(22) Filed: Mar. 23, 2018

(65) Prior Publication Data
US 2018/0230236 A1 Aug. 16, 2018

Related U.S. Application Data

(63) Continuation-in-part of application No. PCT/US2017/060314, filed on Nov. 7, 2017.

(60) Provisional application No. 62/511,535, filed on May 26, 2017, provisional application No. 62/419,788, filed on Nov. 9, 2016.

(51) Int. Cl.
| C07K 16/42 | (2006.01) |
| C07K 14/735 | (2006.01) |
| C07K 19/00 | (2006.01) |
| A61K 39/395 | (2006.01) |
| A61K 45/06 | (2006.01) |
| A61P 37/08 | (2006.01) |
| A61K 39/00 | (2006.01) |

(52) U.S. Cl.
CPC ...... C07K 16/4291 (2013.01); A61K 39/3955 (2013.01); A61K 45/06 (2013.01); C07K 14/70535 (2013.01); C07K 19/00 (2013.01); A61K 2039/505 (2013.01); A61P 37/08 (2018.01); C07K 2317/24 (2013.01); C07K 2317/34 (2013.01); C07K 2317/56 (2013.01); C07K 2317/565 (2013.01); C07K 2317/622 (2013.01); C07K 2317/92 (2013.01); C07K 2319/70 (2013.01)

(58) Field of Classification Search
None
See application file for complete search history.

(56) References Cited

U.S. PATENT DOCUMENTS

| 4,399,216 A | 8/1983 | Axel et al. |
| 4,740,461 A | 4/1988 | Kaufman |
| 4,816,567 A | 3/1989 | Cabilly et al. |
| 4,912,040 A | 3/1990 | Kaufman et al. |
| 4,946,778 A | 8/1990 | Ladner et al. |
| 4,959,455 A | 9/1990 | Clark et al. |
| 5,091,313 A | 2/1992 | Chang |
| 5,254,671 A | 10/1993 | Chang |
| 5,258,498 A | 11/1993 | Huston et al. |
| 5,260,203 A | 11/1993 | Ladner et al. |
| 5,260,416 A | 11/1993 | Chang |
| 5,342,924 A | 8/1994 | Chang et al. |
| 5,428,133 A | 6/1995 | Chang |
| 5,514,776 A | 5/1996 | Chang |
| 5,530,101 A | 6/1996 | Queen et al. |
| 5,585,089 A | 12/1996 | Queen et al. |
| 5,599,677 A | 2/1997 | Dowell et al. |
| 5,614,611 A | 3/1997 | Chang |
| 5,672,480 A | 9/1997 | Dowell et al. |
| 5,693,761 A | 12/1997 | Queen et al. |
| 5,693,762 A | 12/1997 | Queen et al. |
| 5,760,185 A | 6/1998 | Kimachi et al. |
| 5,958,708 A * | 9/1999 | Hardman ............ A61K 47/6873 435/7.21 |
| 5,959,177 A | 9/1999 | Hein et al. |
| 5,994,511 A * | 11/1999 | Lowman ................. A61P 37/06 530/387.3 |
| 6,040,498 A | 3/2000 | Stomp et al. |
| 6,043,345 A | 3/2000 | Saxon et al. |
| 6,180,370 B1 | 1/2001 | Queen et al. |
| 6,267,958 B1 | 7/2001 | Andya et al. |
| 6,423,512 B1 | 7/2002 | Digan et al. |
| 6,504,013 B1 | 1/2003 | Lawton et al. |
| 6,841,659 B2 | 1/2005 | Turpen et al. |
| 6,852,319 B2 | 2/2005 | Hein et al. |
| 6,881,557 B2 | 4/2005 | Foote |

(Continued)

FOREIGN PATENT DOCUMENTS

| CN | 101633698 | 12/2011 |
| JP | H0792167 A | 4/1995 |

(Continued)

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Lloyd et al., Protein Eng Des Sel. Mar. 2009;22(3):159-68. doi: 10.1093/protein/gzn058. Epub Oct. 29, 2008.*
Edwards et al., J Mol Biol. Nov. 14, 2003;334(1):103-18.*
Goel et al., J Immunol. Dec. 15, 2004;173(12):7358-67.*

(Continued)

Primary Examiner — Michael Szperka
(74) Attorney, Agent, or Firm — Myers Bigel, P.A.

(57) ABSTRACT

The present invention provides a chimeric protein comprising: a) a single chain variable fragment (scFv) that binds to a mammalian IgE at an epitope within the amino acid sequence VDGQKATNIFPYTAPGTK (SEQ ID NO:1) of canine IgE or at an epitope within the corresponding amino acid sequence of a different mammalian species; b) a linker peptide; and c) an amino acid sequence comprising an IgE high affinity receptor alpha chain, and methods of use thereof.

28 Claims, 16 Drawing Sheets

Specification includes a Sequence Listing.

(56) References Cited

U.S. PATENT DOCUMENTS

| | | | |
|---|---|---|---|
| 7,148,023 B2 | 12/2006 | Hammerberg | |
| 7,244,580 B2 | 7/2007 | Gershwin et al. | |
| 7,247,711 B2 | 7/2007 | Benson et al. | |
| 7,261,890 B2 | 8/2007 | Krah, III et al. | |
| 7,384,633 B2* | 6/2008 | Sugimura | C07K 16/283 424/142.1 |
| 7,470,773 B2 | 12/2008 | Hammerberg | |
| 7,736,648 B2 | 6/2010 | Kauvar et al. | |
| 7,781,647 B2 | 8/2010 | Bakker et al. | |
| 7,816,334 B2 | 10/2010 | Rice et al. | |
| 7,867,494 B2* | 1/2011 | Liu | A61P 11/00 424/133.1 |
| 7,897,153 B1 | 3/2011 | Braren et al. | |
| 7,910,702 B2 | 3/2011 | Kav et al. | |
| 7,943,144 B2 | 5/2011 | Brown et al. | |
| 8,017,146 B2 | 9/2011 | Stefano et al. | |
| 8,025,898 B2 | 9/2011 | Houze et al. | |
| 8,036,738 B2 | 10/2011 | Sirkar et al. | |
| 8,041,421 B2 | 10/2011 | Birchall et al. | |
| 8,043,250 B2 | 10/2011 | Xu | |
| 8,043,830 B2 | 10/2011 | Barat et al. | |
| 8,067,005 B1 | 11/2011 | Chapman et al. | |
| 8,071,097 B2* | 12/2011 | Wu | A61P 37/08 424/144.1 |
| 8,071,333 B2 | 12/2011 | Giles-Komar et al. | |
| 8,076,456 B2 | 12/2011 | Mattson et al. | |
| 8,080,249 B2* | 12/2011 | Risk | A61K 39/39566 424/153.1 |
| 8,097,704 B2 | 1/2012 | Kim et al. | |
| 8,101,175 B1 | 1/2012 | Croft et al. | |
| 8,101,184 B2 | 1/2012 | Li et al. | |
| 8,101,423 B2 | 1/2012 | Cunningham et al. | |
| 8,101,727 B2 | 1/2012 | Stover et al. | |
| 8,105,598 B2 | 1/2012 | Dimitrov et al. | |
| 8,252,907 B2 | 8/2012 | Krah, III et al. | |
| 8,460,664 B2* | 6/2013 | Chang | A61P 37/00 424/139.1 |
| 9,546,219 B2* | 1/2017 | Hammerberg | C07K 16/4291 |
| 2002/0107359 A1 | 8/2002 | Hogarth et al. | |
| 2003/0190318 A1 | 10/2003 | Torigoe et al. | |
| 2003/0229021 A1 | 12/2003 | Krah, III et al. | |
| 2007/0161066 A1 | 7/2007 | Hammerberg | |
| 2009/0117124 A1 | 5/2009 | Liu et al. | |
| 2009/0252732 A1 | 10/2009 | Siadak et al. | |
| 2010/0040606 A1 | 2/2010 | Lantto et al. | |
| 2010/0040619 A1 | 2/2010 | Li et al. | |
| 2010/0061988 A1 | 3/2010 | Hansen | |
| 2010/0129380 A1 | 5/2010 | McKenzie et al. | |
| 2013/0171137 A1 | 7/2013 | Mitre et al. | |
| 2014/0286958 A1 | 9/2014 | Bammert et al. | |
| 2015/0010547 A1 | 1/2015 | Hammerberg | |
| 2015/0344581 A1 | 12/2015 | Bilsborough | |
| 2016/0280799 A1 | 9/2016 | Bouche et al. | |
| 2018/0230236 A1 | 8/2018 | Hammerberg et al. | |
| 2021/0009678 A1 | 1/2021 | Hammerberg et al. | |

FOREIGN PATENT DOCUMENTS

| | | | |
|---|---|---|---|
| WO | 88/01649 | 3/1988 | |
| WO | WO-9804718 A1 * | 2/1998 | ....... C07K 14/70535 |
| WO | 2006/048781 | 5/2006 | |
| WO | 2008106980 | 9/2008 | |
| WO | WO-2013119419 A1 * | 8/2013 | ......... C07K 16/4291 |
| WO | 2014201525 | 12/2014 | |
| WO | 2015/03406 | 1/2015 | |
| WO | 2016/133197 | 8/2016 | |
| WO | 2019183437 A1 | 9/2019 | |

OTHER PUBLICATIONS

Kanyavuz et al., Nat Rev Immunol. Jun. 2019;19(6):355-368. doi: 10.1038/S41577-019-0126-7.*

Boyce, T.G., Gastroenteritis, from Merck Manuals Professional Edition, downloaded Mar. 22, 2021 from merckmanuals.com/professional/gastrointestinal-disorders/gastroenteritis, 7 pages.*

Tierney, D. and Nardell, E.A., Tuberculosis, from Merck Manuals Professional Edition, downloaded Mar. 22, 2021 from www.merckmanuals.com/professional/infectious-diseases/mycobacteria/tuberculosis-tb, 14 pages.*

Ames et al. "Omalizumab" Nature Reviews Drug Discovery, 3(3):199-200 (2004).

Bird et al. "Single-Chain Antigen-Binding Proteins" Science, 242(4877):423-426 (1988).

Corren et al. "Effects of omalizumab, a humanized monoclonal anti-IgE antibody, on nasal reactivity to allergen and local IgE synthesis" Annals of Allergy, Asthma & Immunology, 93(3):243-248 (2004).

De Graaf et al. "Expression of scFvs and scFv Fusion Proteins in Eukaryotic Cells" Methods in Molecular Biology, 178:379-387 (2002).

European Medicines Agency "Assessment report: Dupixent" EMA/512262/2017 Committee for Medicinal Products for Human Use (CHMP) (100 pages) (Jul. 20, 2017).

GenBank Accession No. S26468 "Ig heavy chain V region—mouse" NCBI (2 pages) (Jul. 23, 1999).

Gunneriusson et al. "Surface Display of a Functional Single-Chain Fv Antibody on *Staphylococci*" Journal of Bacteriology, 178(5):1341-1346 (1996).

Huston et al. "Protein engineering of antibody binding sites: Recovery of specific activity in an anti-digoxin single-chain Fv analogue produced in *Escherichia coli*" Proceedings of the National Academy of Sciences, 85:5879-5883 (1988).

International Preliminary Report on Patentability corresponding to International Patent Application No. PCT/US2017/060314 (7 pages) (dated May 23, 2019).

Janeway et al. "Immunobiology: The Immune System in Health and Disease" Part II: The Recognition of Antigen, pp. 3:1-3:11 (1997).

Jones et al. "Replacing the complementarity-determining regions in a human antibody with those from a mouse" Nature, 321:522-525 (1986).

Kostelny et al. "Formation of a Bispecific Antibody by the Use of Leucine Zippers" The Journal of Immunology, 148(5):1547-1553 (1992).

Kriangkum et al. "Bispecific and bifunctional single chain recombinant antibodies" Biomolecular Engineering, 18:31-40 (2001).

Lantto et al. "Chain Shuffling to Modify Properties of Recombinant Immunoglobulins" Methods in Molecular Biology, 178:303-316(2002).

Maniatis et al. "Regulation of Inducible and Tissue-Specific Gene Expression" Science, 236(4806):1237-1245 (1987).

Marks et al. "By-Passing Immunization: Building High Affinity Human Antibodies by Chain Shuffling" Bio/Technology, 10:779-783 (1992).

Morrison et al. "Chimeric human antibody molecules: Mouse antigen-binding domains with human constant region domains" Proceedings of the National Academy of Sciences, 81:6851-6855 (1984).

Riechmann et al. "Reshaping human antibodies for therapy" Nature, 332:323-327 (1988).

Rudikoff et al. "Single amino acid substitution altering antigen-binding specificity" Proceedings of the National Academy of Sciences, 79:1979-1983 (1982).

Songsivilai et al. "Bispecific antibody: a tool for diagnosis and treatment of disease" Clinical & Experimental Immunology, 79:315-321 (1990).

Verhoeyen et al. "Reshaping Human Antibodies: Grafting an Antilysozyme Activity" Science, 239(4847):1534-1536 (1988).

Voss et al. "The role of enhancers in the regulation of cell-type-specific transcriptional control" Trends in Biochemical Sciences, 11:287-289 (1986).

Ward et al. "Binding activities of a repertoire of single immunoglobulin variable domains secreted from *Escherichia coli*" Nature, 341:544-546 (1989).

Wenzel et al. "Dupilumab efficacy and safety in adults with uncontrolled persistent asthma despite use of medium-to-high-dose inhaled

(56) References Cited

OTHER PUBLICATIONS corticosteroids plus a long-acting beta2 agonist: a randomised double-blind placebo-controlled pivotal phase 2b dose-ranging trial" The Lancet, 388(10039):31-44 (2016).

Dog Purified Immunoglobulin, BethyLaboratories, Medline, 2 pages (2004).

Cretien et al. "A Monoclonal Anti-IgE Antibody Against An Epitope (Amino Acids 367-376) in the CH3 Domain Inhibits IgE Binding to the Low Affinity IgE Receptor (CD23)" The Journal of Immunology, 141(9):3128-3134 (1988).

Griot-Wenk et al. "Characterization of two dog IgE-specific antibodies elicited by different recombinant fragments of the epsilon chain in hens" Veterinary Immunology and Immunopathology, 64:15-32 (1998).

Hammerberg et al. "Auto IgG anti-IgE and IgG X IgE Immune Complex Presence and Effects on ELISA-Based Quantitation of IgE in Canine Atopic Dermatitis, Demodectic Acariasis and Heiminthiasis" Veterinary Immunology and Immunopathology, 60:33-46 (1997).

International Search Report for International Patent Application No. PCT/US04/03566, 8 pages, dated Apr. 20, 2005.

Kalina et al. "IgE ELISA Using Antisera Derived from Epsilon Chain Antigenic Peptides Detects Allergen-Specific IgE in Allergic Horses" Veterinary Immunology and Immunopathology, 92:137-147 (2003).

Kuby "Immunology" Second Edition, pp. 86-96 (1994).

Orton et al. "Canine IgE Monoclonal Antibody Specific for a Filarial Antigen; Production by a Canine X Murine Heterohybridoma Using B Cells from a Clinically Affected Lymph Node" Immunology, 85(3):429-34 (1995).

Vernersson et al. "Cloning, Structural Analysis, and Expression of the Pig IgE EChain" Immunogenetics, 46:461-468 (1997).

"Welcome to UniCAP® InvitroSight(TM) version 3.1, an Interactive Allergy Testing Information and Know-How Service from Pharmacia Diagnostics" Pharmacia Diagnostics AB, 7 pages (2002).

William H. Wong, Ph.D. "Allergen Specific IgE" Technical Bulletin, Diagnostic Laboratory Services Inc., 7 pages (1996).

Written Opinion and International Search Report corresponding to International Patent Application No. PCT/US2017/060314, 10 pages, dated Jan. 23, 2018.

Hammerberg et al. "Therapeutic anti-IgE monoclonal antibody single chain variable fragment (scFv) safety and immunomodulatory effects after one time injection in four dogs" Vet Dermatol., 28(1):52-e13 (2016).

Blubaugh et al. "The anti-inflammatory effects of topical tofacitinib on immediate and late-phase cutaneous allergic reactions in dogs: a placebo-controlled pilot study" Vet. Dermatol., 2 pages (2018) (Abstract only).

Hunter et al. "Generation of canine-human Fc IgE chimeric antibodies for the determination of the canine IgE domain of interaction with FcεRIalpha" Molecular Immunology, 45:2262-2268 (2008) (Abstract only).

Huston et al. "Protein Engineering of Single-Chain Fv Analogs and Fusion Proteins" Methods In Enzymology, 203:46-88 (1991) (Abstract only).

Vangelista et al. "A minimal receptor-Ig chimera of human FcεRI alpha-chain efficiently binds secretory and membrane IgE" Protein Engineering, Design and Selection, 15(1):51-57 (2002).

Jackson et al. "IgE is present on peripheral blood moncytes and B cells in normal dogs and dogs with atopic dermatitis but there is no correlation with serum IgE concentrations" Vet Immunol Immunopathol., 85(3-4):225-232 (2002).

Extended European Search Report corresponding to European Patent Application No. 17869504.5 (12 pages) (dated Jun. 12, 2020).

Hashiguchi et al. "Human FcεRIa-Specific Human Single-Chain Fv (scFv) Antibody with Antagonistic Activity toward IgE/FcεRIa-Binding" Journal of Biochemistry, 133(1):43-49 (2003).

Eggel et al. "Inhibition of Ongoing Allergic Reactions Using a Novel anti-IgE DARPin-Fc Fusion Protein" Allergy, 66(7):961-968 (2011).

Dehlink et al. "A Soluble Form of the High Affinity IgE Receptor, Fc-epsilon-RI, Circulates in Human Serum" PLoS One, 6(4):e19098 (Apr. 2011).

Bachmann et al. "Vaccination against IL-31 for the treatment of atopic dermatitis in dogs" Journal of Allergy and Clinical Immunology, 142:279-281 (2018).

Brunner et al. "Early-onset pediatric atopic dermatitis is characterized by TH2/TH17/TH22-centered inflammation and lipid alterations" Journal of Allergy and Clinical Immunology, 141(6):2094-2106 (2018).

Favrot et al. "A prospective study on the clinical features of chronic canine atopic dermatitis and its diagnosis" Veterinary Dermatology, 21:23-31 (2010).

Gavrilova, Tatyana "Immune Dysregulation in the Pathogenesis of Atopic Dermatitis" Dermatitis, 29:57-62 (2018).

Grimstad et al. "Anti-interleukin-31-antibodies ameliorate scratching behavior in NC/Nga mice: a model of atopic dermatitis" Experimental Dermatology, 18:35-43 (2009).

Guttman-Yassky et al. "IL-17C: A Unique Epithelial Cytokine with Potential for Targeting across the Spectrum of Atopic Dermatitis and Psoriasis" Journal of Investigative Dermatology, 138:1467-1469 (2018).

Hashiguchi et al. "Human FcεRIa-Specific Human Single-Chain Fv (scFv) Antibody with Antagonistic Activity toward IgE/FcεRIa-Binding" Journal of Biochemistry, 133(1):43-49 (2003).

Hawro et al. "Interleukin-31 does not induce immediate itch in atopic dermatitis patients and healthy controls after skin challenge" Allergy, 69:113-117 (2014).

Langan et al. "What Is Meant by a "Flare" in Atopic Dermatitis? A Systematic Review and Proposal" Archives of Dermatology, 142:1190-1196 (2006).

Lourenco et al. "Efficacy of proactive long-term maintenance therapy of canine atopic dermatitis with 0.0584% hydrocortisone aceponate spray: a double-blind placebo controlled pilot study" Veterinary Dermatology, 27:88-e25 (2016).

Maddox et al. "Elevated Serum Levels in Human Pregnancy of a Molecule Immunochemically Similar to Eosinophil Granule Major Basic Protein" Journal of Experimental Medicine, 158:1211-1226 (1983).

Marsella et al. "Cellular and cytokine kinetics after epicutaneous allergen challenge (atopy patch testing) with house dust mites in high-IgE beagles" Veterinary Dermatology, 17:111-120 (2006).

Monino-Romero et al. "Soluble FcεRI: A biomarker for IgE-mediated diseases" Allergy, 74(7):1381-1384 (2019).

Noda et al. "The Asian atopic dermatitis phenotype combines features of atopic dermatitis and psoriasis with increased TH17 polarization" Journal of Allergy and Clinical Immunology, 136(5):1254-1264 (2015).

Olivry et al. "Early Activation of Th2/Th22 Inflammatory and Pruritogenic Pathways in Acute Canine Atopic Dermatitis Skin Lesions" Journal of Investigative Dermatology, 136:1961-1969 (2016).

Olivry et al. "Investigations on the role of nerve growth factor in dogs with atopic dermatitis" Free Communication Abstracts: Friday Morning, Jun. 3rd, Session 8: Allergic Diseases: Pathobiology (Pathogenesis and Diagnosis) (FC54-62) (2016).

Olivry et al. "Stratum corneum removal facilitates experimental sensitization to mite allergens in atopic dogs" Veterinary Dermatology, 22:188-196 (2010).

Olivry et al. "Treatment of canine atopic dermatitis: 2015 updated guidelines from the international committee on allergic diseases of animals (ICADA)" BMC Veterinary Research, 11(210):1-15 (2015).

Paps et al. "Development of an Allergen-induced Atopic Itch Model in Dogs: A Preliminary Report" Acta Dermato-Venereologica, 96:400-401 (2016).

Pucheu-Haston et al. "Review: Lymphocytes, cytokines, chemokines and the T-helper 1—T-helper 2 balance in canine atopic dermatitis" Veterinary Dermatology, 26:124-e32 (2015).

Steffan et al. "Remission of the clinical signs of atopic dermatitis in dogs after cessation of treatment with cyclosporin A or methylprednisolone" Veterinary Record, 154:681-684 (2004).

(56) References Cited

OTHER PUBLICATIONS

Takamori et al. "IL-31 is crucial for induction of pruritus, but not inflammation, in contact hypersensitivity" Scientific Reports, 8(6639):1-11 (2018).
Tamamoto-Mochizuki et al. "Proactive maintenance therapy of canine atopic dermatitis with the anti-IL-31 lokivetmab. Can a monoclonal antibody blocking a single cytokine prevent allergy flares?" Veterinary Dermatology, 30 (2):98-e26 (2019).
Tang et al. "Are the concepts of induction of remission and treatment of subclinical inflammation in atopic dermatitis clinically useful?" Journal of Allergy and Clinical Immunology, 133:1615-1625 (2014).
Thomas et al. "Validation of Treatment Escalation as a Definition of Atopic Eczema Flares" PLoS One, 10(4) e0124770(2015).
Weidinger et al. "Atopic dermatitis" Nature Reviews Disease Primers, 4(1):1-20 (2018).
Wilhelm et al. "Breed-associated phenotypes in canine atopic dermatitis" Veterinary Dermatology, 22:143-149 (2010).

\* cited by examiner scFv-5.91 Amino Acid Sequence
* Variable Heavy Chain [Italic Letters]
* Variable Light Chain [Bold Letters]
* Linker [Underlined Letters]
* CDRs [Highlighted]

*EVQLQQSGPELVKPGASMKISCKASGYSITGYTIHWVKQSHGKNLEWIGL*
*INPYTGGITYNQNFKGKATLTVDKSSTAYMELLSLTSEDSAVYYCSRGP*
*YGNFYAMDYWGQGTSVTVSS*<u>GGGGSGGGGSGGGGS</u>DIQMTQSPASL
SASVGETVTITCRASGNIHNYLAWYQQKQGKSPQLLVYNAKTLADSVPS
RFSGSGSGTQFSLKINSLQPEDFGSYYCQHFWSTPYTFGGGTKLEIKRA

FIG. 2

Chimera of FcεRI-alpha chain x scFv-5.91 Amino Acid Sequence
* FcεRI-alpha chain [Black Letters]
* Linkers [Underlined Letters]
* scFv-5.91 Variable Heavy Chain [Italic Letters]
* scFv-5.91 Variable Light Chain [Bold Letters]
* CDRs [Highlighted]

DTLKPTVSMNPPWNTILKDDSVTLTCTGNNSLEVDSAVWLHNNTTLQETT
SRLDINKAQIQDSGEYRCRENRSILSDPVYLTVFTEWLILQASANVVMEGE
SFLIRCHSWKNLRLTKVTYYKDGIPIRYWYENFNISISNVTTKNSGNYSCS
GQIQQKGYTSKVLNIIVKKEPTKQNKYSGL<u>QGGGGSGGGGSGGGGS</u>*EV*
*QLQQSGPELVKPGASMKISCKASGYSITGYTIHWVKQSHGKNLEWIGLIN*
*PYTGGITYNQNFKGKATLTVDKSSTAYMELLSLTSEDSAVYYCSRGPYG*
*NFYAMDYWGQGTSVTVSS*<u>GGGGSGGGGSGGGGS</u>DIQMTQSPASLSA
SVGETVTITCRASGNIHNYLAWYQQKQGKSPQLLVYNAKTLADSVPSRF
SGSGSGTQFSLKINSLQPEDFGSYYCQHFWSTPYTFGGGTKLEIKRA

FIG. 3

Clinical Response of 2 Dogs to Subcutaneous injection of 3 mg/ml of Anti-IgE scFv-5.91 x FcɛRI alpha chain chimera at 2 mg/Kg

- Heart rate- no change during 60 m post injection
- Respiratory rate - no change during 60 m post injection
- Mucous membrane reperfusion - no change during 60 m post injection
- Rectal temperature - no change during 60 m post injection
- Gastrointestinal - no vomiting or diarrhea during 24 h post injection
- Attitude/appetite - no change during 24 h post injection

*FIG. 7* ing herein by reference into the specification for its disclosures.

TREATMENT OF ALLERGIC DISEASES WITH CHIMERIC PROTEIN

PRIORITY STATEMENT

This application is a continuation-in-part application of, and claims priority to, International Application No. PCT/US2017/060314 filed on Nov. 7, 2017, which claims the benefit, under 35 U.S.C. § 119(e), of U.S. Provisional Application Ser. No. 62/419,788, filed Nov. 9, 2016, and U.S. Provisional Application Ser. No. 62/511,535, filed May 26, 2017, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5051-905IP_ST25.txt, 15,866 bytes in size, generated on Nov. 30, 2020, and filed via EFS-Web, is provided in lieu of a paper copy. This Sequence Listing is hereby incorporated herein by reference into the specification for its disclosures.

FIELD OF THE INVENTION

The present invention is directed to a chimeric protein useful for treating IgE-related disorders in mammalian subjects, particularly veterinary subjects, along with methods of making and using the same.

BACKGROUND OF THE INVENTION

Allergic disorders are currently the 6th leading cause of chronic illness in the U.S. and are steadily increasing every year. Studies have shown that as many as 30% of adults and 40% of children in the U.S. are currently afflicted with an allergic disorder. Allergic disorders also account for about 25% of all visits to the veterinarian for dogs and cats. For example, canine atopic dermatitis in dogs is the second most common allergic skin condition affecting about 10-15% of animals. Treatment of recurring dermatitis in dogs frequently results in less than optimal outcomes. When the disease can be linked to exposure to specific allergens, such as house dust mites, desensitization injections can be effective in some individuals when carried out over an extended time; however, most cases are not resolved by desensitization and require a combination of allergen avoidance and anti-inflammatory drugs. The prolonged use of these drugs, such as corticosteroids, can result in severe side effects. These same challenges exist for human allergy sufferers.

The present invention overcomes previous shortcomings in the art by providing a chimeric protein comprising a) a single chain variable fragment (scFv) that binds to IgE at an epitope corresponding to the amino acid sequence VDGQKATNIFPYTAPGTK (SEQ ID NO:1); b) a linker peptide; and c) an amino acid sequence comprising an IgE high affinity receptor alpha chain, in particular the extracellular segment of the IgE high affinity receptor alpha chain.

SUMMARY OF THE INVENTION

In one aspect, the present invention provides a chimeric protein comprising: a) a single chain variable fragment (scFv) that binds to a mammalian IgE at an epitope within the amino acid sequence VDGQKATNIFPYTAPGTK (SEQ ID NO:1) of canine IgE or at an epitope within the corresponding amino acid sequence of a different mammalian species; b) a linker peptide; and c) an amino acid sequence comprising an IgE high affinity receptor alpha chain (e.g., the extracellular segment of the IgE high affinity receptor alpha chain). In some embodiments, the scFv binds to human IgE at an epitope within the amino acid sequence EDGQVMDVDLSTASTTQ (SEQ ID NO:15). In some embodiments, the scFv binds to equine IgE at an epitope within the amino acid sequence IDGQKVD-EQFPTQHGVKQ (SEQ ID NO:16) and in some embodiments, the scFv binds to feline IgE at an epitope within the amino acid sequence VDGQKATNIFPYTAPGKQ (SEQ ID NO:17).

In a further aspect, the present invention provides a recombinant nucleic acid sequence encoding the chimeric protein of this invention.

In another aspect, the present invention provides a method of reducing free serum IgE levels in a mammalian subject in need thereof, comprising administering said subject the chimeric protein of this invention in an amount effective to reduce free serum IgE levels in said subject.

The invention additionally provides a method of preventing/delaying/reducing/inhibiting an allergic disorder, in a mammalian subject in need thereof, the method comprising administering to the subject a composition comprising a therapeutically effective amount of an anti-IgE biologic agent that binds to immunoglobulin E (IgE) in the early phase of inflammation, wherein the subject is asymptomatic or paucisymptomatic (i.e., "clear" or "almost clear") with or without currently receiving an anti-inflammatory agent, an anti-allergy agent, an immunomodulatory agent or a combination thereof.

The present invention is explained in greater detail in the drawings herein and the specification set forth below. The disclosures of all patent and nonpatent publications and references cited herein are incorporated by reference herein in their entirety.

BRIEF DESCRIPTION OF THE DRAWINGS

FIG. 2. scFv-5.91 amino acid sequence (SEQ ID NO:8).

FIG. 3. Chimera of FcεRI-alpha chain×scFv-5.91 amino acid sequence (SEQ ID NO:14).

FIG. 7. Improved reduction of circulating IgE by scFv-5.91×FcεRI alpha chain chimera compared to scFv-5.91 PEG after single injection treatment in reduction-resistant dogs.

DETAILED DESCRIPTION OF THE INVENTION

Figure 1:
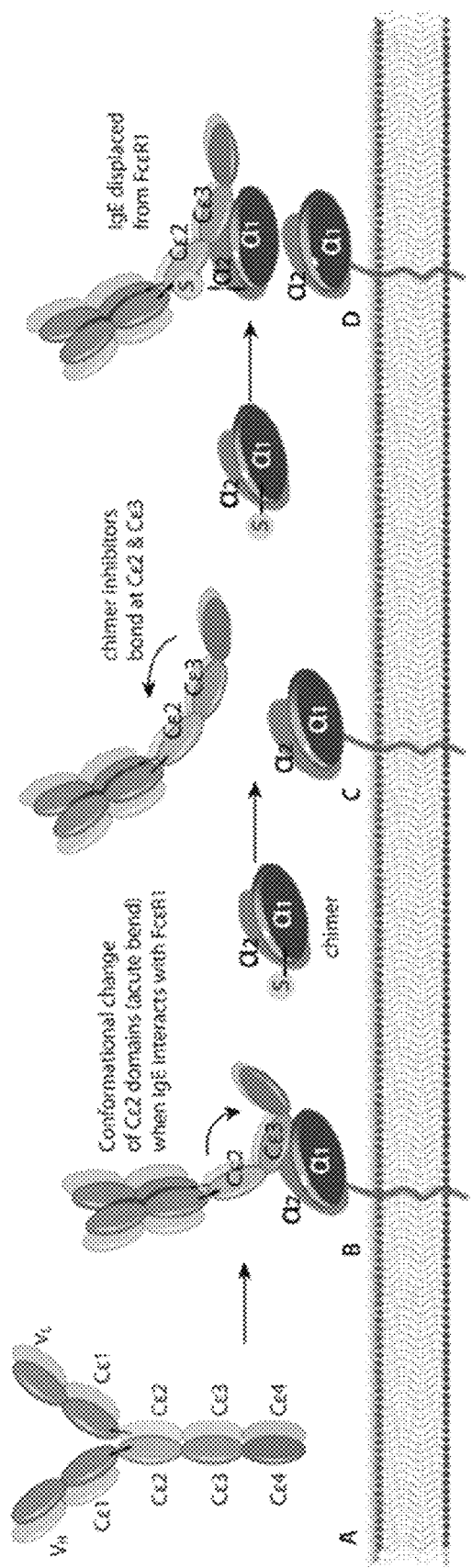
FIG. 1. The chimera of scFv 5.91 specific for an epitope in the Cε2 domain of IgE (circle with S) linked to the alpha chain portion of the high affinity receptor for IgE binds free IgE to block activation of mast cells and basophils, as well as displacing IgE already bound to these cells.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

All publications, patent applications, patents, patent publications and other references cited herein are incorporated by reference in their entireties for the teachings relevant to the sentence and/or paragraph in which the reference is presented.

The invention, in part, relates to methods of using anti-IgE biologic agents in the treatment of allergic diseases and disorders. Allergic diseases and disorders typically have an inflammatory component associated with the disease or disorder which, in part, is the cause for some or all of the symptoms experienced by patients afflicted with an allergic disease or disorder. In general, the inflammatory component is due to the body's reaction towards an allergen triggering an inflammatory cascade. The inflammatory cascade consists of an early phase inflammatory reaction and a late phase inflammatory reaction.

The early phase inflammatory reaction occurs within minutes of allergen exposure and mainly reflects the secretion of mediators by mast cells at the affected site. In sensitized individuals, these mast cells already have allergen-specific IgE bound to their surface high-affinity IgE receptors (FcεRI). When crosslinking of adjacent IgE molecules by bivalent or multivalent allergen occurs aggregation of FcεRI triggers a complex intracellular signaling process that results in the secretion of various pre-formed inflammatory mediators which contribute of the acute signs and symptoms associated with early phase inflammatory response. In the late phase inflammatory reaction mast cells responding to IgE and allergen also release a broad range of newly synthesized cytokines, chemokines, and growth factors, but the are released more slowly than the pre-formed inflammatory mediators and contribute the signs and symptoms associated with late phase inflammatory response. Thus, developing agents which inhibit the function of IgE in the early and/or late phase inflammatory reaction could modulate the inflammatory cascade present in allergic diseases or disorders.

In some embodiments, the present invention provides an anti-IgE biologic agent to modulate the function of IgE in the early phase of the inflammatory cascade. This anti-IgE biologic agent of the invention can be any agent that is produced by means of biological processes involving recombinant DNA technology. For example, in some embodiments, the anti-IgE biologic agent is an anti-IgE monoclonal antibody, an anti-IgE chimeric biologic agent, or a vaccine designed to induce an anti-IgE antibody response. In one embodiment, the anti-IgE biologic agent is an anti-IgE chimeric biologic agent, such as, e.g., the chimeric protein discussed in more detail below. In some embodiments, the anti-IgE biologic agent is a monoclonal antibody or fragments thereof. In some embodiments, the anti-IgE biologic agent is anti-IgE monoclonal antibody omalizumab.

In particular, one aspect of the invention is based on the discovery and development of a chimeric protein as a therapeutic, i.e., anti-IgE chimeric biologic agent, for allergic diseases and disorders. Specifically, a chimera of anti-IgE scFv linked to recombinant high affinity receptor alpha chain (FcεRI) was developed in order to increase the affinity of the therapeutic anti-IgE peptide and increase blocking of IgE binding to mast cells and basophils. This chimeric protein shows a marked increase in binding affinity to IgE as well as the ability to block IgE binding to mast cells. In vitro testing with canine mast cells and with canine lymph node B cells has shown that this chimera blocks IgE binding to mast cells and causes IgE-bearing B cell anergy. This chimera can be used to block the sensitization of mast cells by IgE and therefore acts as an immunotherapeutic agent to provide rapid alleviation and long-term control of clinical signs of atopic dermatitis in dogs and could be adapted for use in humans to treat allergic conditions and disease (e.g., hay fever, eczema, food allergy).

The chimeric protein (e.g., anti-IgE chimeric biologic agent) of this invention demonstrated an unexpected ability to desensitize inflammatory cells bearing IgE by removing surface bound IgE. Rapid desensitization of inflammatory cells is a major improvement in the properties of anti-IgE antibody therapies such as Xolair®. Current anti-IgE therapies block IgE binding to inflammatory cells but do not stop inflammatory reactions by pre-sensitized cells which can be long-lived. Thus this chimeric protein offers immediate relief from clinical disease signs not provided by current anti-IgE therapies. Also, this chimeric protein showed IgE blocking ability far exceeding that of previous anti-IgE antibodies in dogs resistant to this therapeutic approach.

Thus, in one embodiment, the present invention provides a chimeric protein (e.g., anti-IgE chimeric biologic agent) comprising: a) a single chain variable fragment (scFv) that binds to IgE at an epitope corresponding to amino acids 146 to 162 thereof (VDGQKATNIFPYTAPGTK, SEQ ID NO:1); b) a linker peptide; and c) an amino acid sequence comprising an IgE high affinity receptor alpha chain.

In a further embodiment, the present invention provides a chimeric protein comprising: a) a single chain variable fragment (scFv) that binds to a mammalian IgE at an epitope within the amino acid sequence VDGQKATNIFPYTAPGTK (SEQ ID NO:1) of canine IgE or at an epitope within the corresponding amino acid sequence of a different mammalian species; b) a linker peptide; and c) an amino acid sequence comprising an IgE high affinity receptor alpha chain. In some embodiments, the scFv binds to human IgE at an epitope within the amino acid sequence EDGQVMDVDLSTASTTQ (SEQ ID NO:15). In some embodiments, the scFv binds to equine IgE at an epitope within the amino acid sequence IDGQKVDEQFPTQHGVKQ (SEQ ID NO:16) and in some embodiments, the scFv binds to feline IgE at an epitope within the amino acid sequence VDGQKATNIFPYTAPGKQ (SEQ ID NO:17).

In one embodiment, the scFv can comprise, consist essentially of and/or consist of: (i) a light chain (LC) variable region having at complementarity determining regions (CDRs) thereof at least one, two, or all three of the amino acid sequences of RASGNIHNYL (LC CDR1; SEQ ID NO:2); NAKTLAD (LC CDR2; SEQ ID NO:3); and FWSTPYT (LC CDR3; SEQ ID NO:4); and/or (ii) a heavy chain (HC) variable region having at complementarity determining regions (CDRs) thereof at least one, two, or all three of the amino acid sequences of: GYTIH (HC CDR1; SEQ ID NO:5); LINPYTGGITYNQNFKGKAT (HC CDR2; SEQ ID NO:6); and GPYGNFYAMDY (HC CDR3; SEQ ID NO:7).

In one embodiment, the scFv can comprise the amino acid sequence:

(SEQ ID NO: 8)
EVQLQQSGPELVKPGASMKISCKASGYSITGYTIHWVKQSHGKNLEW

IGLINPYTGGITYNQNFKGKATLTVDKSSSTAYMELLSLTSEDSAVY

YCSRGPYGNFYAMDYWGQGTSVTVSSGGGGSGGGGSGGGGSDIQMTQ

SPASLSASVGETVTITCRASGNIHNYLAWYQQKQGKSPQLLVYNAKT

LADSVPSRFSGSGSGTQFSLKINSLQPEDFGSYYCQHFWSTPYTFGG

GTKLEIKRA.

The chimeric protein of this invention can comprise a linker peptide to link the scFv to the IgE high affinity receptor alpha chain. In some embodiments, the linker peptide can comprise (GGGS)n (SEQ ID NO:18) subunits in any combination and n can be 1 or any number greater than 1 (e.g., 2, 3, 4, 5, 6, 7, 8, 9, 10, 11, 12, 13, 14, 15, 16, 17, 18, 19, 20, 25, 30, 35, 40, 45, 50, etc. In some embodiments, the linker peptide can comprise, consist essentially of, or consist of the amino acid sequence: GGGGSGGGGSGGGGS (SEQ ID NO:9).

In some embodiments of this invention, the IgE high affinity receptor alpha chain can comprise, consist essentially of or consist of the following amino acid sequence:

A) High affinity immunoglobulin epsilon receptor subunit alpha precursor [*Homo sapiens*]. NCBI Reference Sequence: NP_001992.1

(SEQ ID NO: 10)
VPQKPKVSLNPPWNRIFKGENVTLTCNGNNFFEVSSTKWFHNGSLSE

ETNSSLNIVNAKFEDSGEYKCQHQQVNESEPVYLEVFSDWLLLQASA

EVVMEGQPLFLRCHGWRNWDVYKVIYYKDGEALKYWYENHNISITNA

TVEDSGTYYCTGKVWQLDYESEPLNITVIKAPREKYWLQ

B) High affinity immunoglobulin epsilon receptor subunit alpha precursor [*Canis lupus familiaris*]. NCBI Reference Sequence: NP_001104236.2

(SEQ ID NO: 11)
DTLKPTVSMNPPWNTILKDDSVTLTCTGNNSLEVDSAVWLHNNTTLQ

ETTSRLDINKAQIQDSGEYRCRENRSILSDPVYLTVFTEWLILQASA

NVVMEGESFLIRCHSWKNLRLTKVTYYKDGIPIRYWYENFNISISNV

TTKNSGNYSCSGQIQQKGYTSKVLNIIVKKEPTKQNKYSGLQ

C) High affinity immunoglobulin epsilon receptor subunit alpha [*Felis catus*]. NCBI
Reference Sequence: XP_006943111.1

(SEQ ID NO: 12)
GTREPTVSLNPPWTTILKEDSVTLTCKENNSLELNSTVWFHNKTKLG

VTTLTLDIVKAQIRDSGEYTCQNKGSMLSKPVSLKVFREWLLLQAST

EVVLEGESFLIRCHSWRNLNVKKVTYYRNGKFLQFWYDNYNITINNA

TETDSGTYYCTGWISKQNHISNFLNIVVRKDSPPEHQSKYYWLQ

D) High affinity immunoglobulin epsilon receptor subunit alpha precursor [*Equus caballus*]. NCBI Reference Sequence: NP_001093237.1

(SEQ ID NO: 13)
AIRKSTVSLNPPWNRIFRGENVTLTCNKNKPLKGNSTEWTYNNTTLE

VTTSSLNITNASHRSSGEYRCRNNDLNLSEAVHLEVFSDWLLLQASA

EEVIEGKALVLRCRGWKDWDVFKVIYYKDGKPLEYWYENKNISIESA

TTENSGTYYCEGAFNFKRTSERYTSDYLNITVKKAEQSKRYWLQ.

In one embodiment, the chimeric protein of this invention can comprise, consist essentially of, or consist of the amino acid sequence:

(SEQ ID NO: 14)
DTLKPTVSMNPPWNTILKDDSVTLTCTGNNSLEVDSAVWLHNNTTLQ

ETTSRLDINKAQIQDSGEYRCRENRSILSDPVYLTVFTEWLILQASA

NVVMEGESFLIRCHSWKNLRLTKVTYYKDGIPIRYWYENFNISISNV

TTKNSGNYSCSGQIQQKGYTSKVLNIIVKKEPTKQNKYSGLQGGGGS

GGGGSGGGGSEVQLQQSGPELVKPGASMKISCKASGYSITGYTIHWV

KQSHGKNLEWIGLINPYTGGITYNQNFKGKATLTVDKSSSTAYMELL

SLTSEDSAVYYCSRGPYGNFYAMDYWGQGTSVTVSSGGGGSGGGGSG

GGGSDIQMTQSPASLSASVGETVTITCRASGNIHNYLAWYQQKQGKS

PQLLVYNAKTLADSVPSRFSGSGSGTQFSLKINSLQPEDFGSYYCQH

FWSTPYTFGGGTKLEIKRA.

The chimeric protein of this invention can be humanized, caninized, felinized, or equinized according to protocols know in the art.

In some embodiments of this invention, the chimeric protein can further comprise a water soluble polyalkylene oxide group or moiety coupled thereto. In particular embodiments, the water soluble polyalkylene oxide group can comprise polyethylene glycol (i.e., the chimeric protein can be "pegylated"). The polyalkylene glycol moiety can be linked or attached or associated with the chimeric protein at either or both ends of the protein.

In some embodiments, the scFv of this invention can form an antigen-binding monomer.

In some embodiments, of this invention, the chimeric protein can bind to canine IgE at a dissociation constant (Kd) not greater than 500 pM, 100 pM or 10 pM.

The present invention further provides a composition comprising the chimeric protein of any preceding claim in a pharmaceutically acceptable carrier.

In another embodiment of this invention, a recombinant nucleic acid molecule (e.g., an isolated recombinant nucleic acid molecule) is provide, which encodes the chimeric protein of this invention. Also provided herein is a composition comprising the recombinant nucleic acid molecule of this invention in a pharmaceutically acceptable carrier.

The present invention additionally provides a host cell containing the recombinant nucleic acid molecule of this invention and expressing the nucleic acid molecule to produce the encoded chimeric protein.

The host cell of this invention can be a bacterial cell, a yeast cell, a mammalian cell in culture; or a plant cell in vitro, in vivo or in planta.

The present invention further comprises methods of using the chimeric protein of this invention. For example, the present invention provides a method of reducing free serum IgE levels in a mammalian subject in need thereof, comprising administering said subject the chimeric protein of any preceding claim or composition of any preceding claim in an amount effective to reduce free serum IgE levels in said subject.

A subject of the methods of this invention can be a human, dog, cat, or horse.

In some embodiments of the methods of this invention, the administering step can be carried out by parenteral injection, topical administration, transdermal administration, oral administration, and/or inhalation administration.

In some embodiments of this invention, the subject is afflicted with atopic dermatitis, allergic rhinitis, asthma, allergic conjunctivitis, urticaria, gastro-intestinal inflammation, and/or oral-pharyngeal inflammation.

The present invention additionally provides a method of preventing/delaying/reducing/inhibiting an allergic disorder, in a mammalian subject in need thereof, the method comprising administering to the subject a composition comprising a therapeutically effective amount of an anti-IgE biologic agent that binds to immunoglobulin E (IgE) in the early phase of inflammation, wherein the subject is asymptomatic or paucisymptomatic with or without currently receiving an anti-inflammatory agent, an anti-allergy agent, an immunomodulatory agent or a combination thereof.

In some embodiments, the anti-inflammatory agent, the anti-allergy agent, and/or the immunomodulatory agent is a glucocorticoid, a non-steroidal anti-inflammatory agent, a leukotriene antagonist, a Janus kinase (JAK) inhibitor, an immunoglobulin, an anti-histamine, an allergen-specific or non-specific immunotherapy agent, and combinations thereof administered by either oral, subcutaneous, intramuscular, intravenous or topical routes. The subject is a canine, feline, equine, or human. For example, a human, dog, cat, or horse.

In some embodiments, the allergic disorder comprises allergic inflammation and/or chronic inflammation. For example, allergic disorder comprises allergic inflammation and is selected from allergic rhinitis, atopic dermatitis, allergic asthma, allergic conjunctivitis, gastro-intestinal inflammation, urticaria, and/or food allergy.

In one embodiment, the allergic disorder is atopic dermatitis and the subject is a dog. In some embodiments, the dog has received and/or is currently receiving, cyclosporine, glucocorticoids, oclacitinib, lokivetmab, allergen-specific immunotherapy agent, non-specific immunotherapy agent, by any route, or a combination thereof.

In some embodiments, the allergic disorder comprises chronic inflammation and is celiac disease, vasculitis, lupus, chronic obstructive pulmonary disease (COPD), irritable bowel disease (IBS), atherosclerosis, arthritis, systemic lupus erythematosus, multiple sclerosis, asthma, chronic peptic ulcer, sinusitis, tuberculosis, rheumatoid arthritis, periodontitis, ulcerative colitis, Crohn's disease, atopic dermatitis (eczema), rosacea, seborrheic dermatitis, and/or psoriasis.

In some embodiments, the anti-IgE biologic agent is an anti-IgE monoclonal antibody or an anti-IgE chimeric biologic or a vaccine designed to induce an anti-IgE antibody response. For example, anti-IgE monoclonal antibodies omalizumab, ligelizumab, and/or XmAb7195.

The present invention additionally provides a method, wherein the anti-IgE chimeric biologic comprises the chimeric protein according to one or more embodiments as described above.

In some embodiments, the anti-IgE biologic agent is administered about every 2 weeks to about 8 weeks. In some embodiments, the anti-IgE biologic agent is administered in combination with an anti-infectious agent. The anti-infectious agent is an antiseptic, an antibiotic, an antifungal, or a combination thereof.

In some embodiments, the allergic disorder is atopic dermatitis, eczema, rosacea, seborrheic dermatitis, and/or psoriasis and the biologic is administered in combination with topical moisturizers and/or baths.

In some embodiments of the invention, the method provides reduced flares, delays relapses and/or recurrences of lesions in a subject with atopic dermatitis.

Definitions

The terms "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" can mean one, two, three, four, five, six, seven, eight, nine, ten or more, up to any number.

The transitional phrase "consisting essentially of" means that the scope of a claim is to be interpreted to encompass the specified materials or steps recited in the claim, and those that do not materially affect the basic and novel characteristics of the claimed invention.

As used herein, the terms "subject" and "patient" are used interchangeably herein and refer to both human and nonhuman animals. A subject of this invention can be any subject that is susceptible to an allergic disorder and in particular embodiments, the subject of this invention is a human subject.

A "subject in need thereof" or "a subject in need of" is a subject known to have, or is suspected of having or developing or is at risk of having or developing an allergic disorder.

An "appropriate therapy" for the treatment of an allergic disorder of this invention includes therapies well known in the art, including but not limited to, anti-inflammatory agents, immunomodulatory agents, and combinations thereof.

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, and/or change in clinical parameters of the condition, disorder, disease or illness, etc., as would be well known in the art.

Additionally as used herein, the terms "proactive," "prevent," "preventing" or "prevention" refer to any type of action that results in the absence, avoidance and/or delay of the onset and/or progression of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, *The Science and Practice of Pharmacy* (latest edition)).

The term "biologically active" as used herein means an enzyme or protein having structural, regulatory, or biochemical functions of a naturally occurring molecule.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

Subjects with which the present invention is concerned include any subject susceptible to an allergic condition or disorder and are, in general, mammalian subjects, including humans, dogs, cats, and horses. The subjects may be of any gender, any ethnicity and any age.

"Therapeutically effective amount" or "treatment effective amount" as used herein refers to the amount of an anti-IgE antibody determined to produce a therapeutic response in a subject. Such therapeutically effective amounts are readily ascertained by one of ordinary skill in the art.

"Canine IgE" is known and described in, for example, U.S. Pat. Nos. 7,261,890 and 6,504,013.

The term "biologic agent" as used herein refers to any pharmaceutical drug product manufactured in, extracted from, or semisynthesized from biological sources. For example, they (or their precursors or components) can be isolated from living sources-human, animal, plant, fungal, or microbial or they can be specifically engineered macromolecular products like proteins-and nucleic acid-based drugs. Different from totally synthesized pharmaceuticals, they can include vaccines (which in some embodiments can be extracted directly from a biological source), blood, blood component, allergenics, somatic cells, gene therapies, tissues, recombinant therapeutic proteins, and living cells used in cell therapy. Biologic agents can be composed of sugars, proteins, and/or nucleic acids, and/or complex combinations of these substances, and/or may be living cells and/or tissues.

"Antibody" as used herein refers to an intact immunoglobulin of any isotype, or a fragment thereof that can compete with the intact antibody for specific binding to the target antigen, and includes chimeric, humanized, caninized, equinized, felinized, fully human, fully canine, fully equine, fully feline, and bispecific or plurispecific antibodies. For example, an IgM monoclonal antibody could have multiple targets. An intact antibody generally will comprise at least two full-length heavy chains and two full-length light chains, but in some instances may include fewer chains such as antibodies naturally occurring in camelids which may comprise only heavy chains. Antibodies according to the invention may be derived solely from a single source, or may be "chimeric," that is, different portions of the antibody may be derived from two different antibodies and/or species. For example, the complementarity determining regions (CDRs) may be derived from a rat or murine source, while the framework region of the V region is derived from a different animal source, including human. The antibodies or binding fragments of the invention may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

"Light chain" as used herein includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains according to the invention include kappa chains and lambda chains.

"Heavy chain" includes a full-length heavy chain and fragments thereof having sufficient variable region sequence to confer binding specificity. A full-length heavy chain includes a variable region domain, $V_H$, and three constant region domains, $C_{H1}$, $C_{H2}$, and $C_{H3}$. The $V_H$ domain is at the amino-terminus of the polypeptide, and the CH domains are at the carboxyl-terminus, with the $C_{H3}$ being closest to the —COOH end. Heavy chains according to the invention may be of any isotype, including IgG (including IgG1, IgG2, IgG3 and IgG4 subtypes), IgA (including $IgA_1$ and $IgA_2$ subtypes), IgM and IgE.

"Immunologically functional fragment" (or simply "fragment") of an immunoglobulin chain, as used herein, refers to a portion of an antibody light chain or heavy chain that lacks at least some of the amino acids present in a full-length chain but which is capable of binding specifically to an antigen. Such fragments are biologically active in that they bind specifically to the target antigen and can compete with intact antibodies for specific binding to a given epitope. In one aspect of the invention, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of intact antibodies. Immunologically functional immunoglobulin fragments of the invention include, but are not limited to, Fab, Fab', F(ab')$_2$, Fv, domain antibodies and single-chain antibodies, and may be derived from any mammalian source, including but not limited to human, mouse, rat, camelid or rabbit. It is contemplated further that a functional portion of the inventive antibodies, for example, one or more CDRs, could be covalently bound to a second protein or to a small molecule to create a therapeutic agent directed to a particular target in the body, possessing bifunctional therapeutic properties, or having a prolonged serum half-life.

"Fab fragment" as used herein is comprised of one light chain and the CHI and variable regions of one heavy chain. The heavy chain of a Fab molecule cannot form a disulfide bond with another heavy chain molecule.

"Fc" region as used herein contains two heavy chain fragments comprising the C.sub.H1 and C.sub.H2 domains of an antibody. The two heavy chain fragments are held together by two or more disulfide bonds and by hydrophobic interactions of the CH3 domains.

"Fab' fragment" contains one light chain and a portion of one heavy chain that contains the $V_H$ domain and the $C_{H1}$ domain and also the region between the $C_{H1}$ and $C_{H2}$ domains, such that an interchain disulfide bond can be formed between the two heavy chains of two Fab' fragments to form a F(ab')$_2$ molecule.

"F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab')2 fragment thus is composed of two Fab' fragments that are held together by a disulfide bond between the two heavy chains.

"Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203, the disclosures of which are incorporated by reference.

"Domain antibody" as used herein is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

"Bivalent antibody" as used herein comprises two antigen binding sites. In some instances, the two binding sites have the same antigen specificities. However, bivalent antibodies may be bispecific (see below).

"Multispecific antibody" as used herein is one that targets more than one antigen or epitope.

"Bispecific," "dual-specific" or "bifunctional" antibody as used herein is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), *Clin. Exp. Immunol.* 79:315-321; Kostelny et al. (1992), *J. Immunol.* 148:1547-1553. The two binding sites of a bispecific antibody will bind to two different epitopes, which may reside on the same or different protein targets.

Antibodies and Immunologically Functional Fragments

As discussed below, a variety of selective binding agents (e.g., anti-IgE chimeric biologic agent) useful for regulating the activity of IgE are provided. These agents include, for instance, antibodies and immunologically functional fragments thereof that contain an antigen binding domain (e.g., single chain antibodies, domain antibodies, immunoadhesions, and polypeptides with an antigen binding region) and specifically bind to a canine IgE.

Variable Domains of Antibodies. Also provided are antibodies that comprise a light chain variable region as described herein, and/or a heavy chain variable region as described herein CDRs of Antibodies. The antibodies and immunological functional fragments that are provided can include one, two, three, four, five or all six of the CDRs listed herein. The heavy and light chain variable regions and the CDRs that are disclosed herein can be used to prepare any of the various types of immunologically functional fragments that are known in the art including, but not limited to, domain antibodies, Fab fragments, Fab' fragments, F(ab')$_2$ fragments, Fv fragments, single-chain antibodies, sdFvs, scFvs, etc.

Single-chain Variable Fragments. Single chain variable fragment (scFv) antibodies can be produced in accordance with known techniques or variations thereof that will be apparent to those skilled in the art. See generally U.S. Pat. No. 4,946,778 to Ladner et al. and U.S. Pat. No. 5,258,498 to Huston and Opperman; see also U.S. Pat. Nos. 8,097,704; 8,043,830; 7,943,144; 7,910,702; and 7,816,334.

Bispecific or Bifunctional Antibodies. The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann, 1990, *Clin. Exp. Immunol.* 79: 315-321; Kostelny et al., 1992, *J. Immunol.* 148: 1547-1553.

Chimeric, Humanized, Caninized, Equinized, and Felinized Antibodies. Chimeric and humanized antibodies based upon the foregoing sequences are also provided.

Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., *Proc. Natl. Acad. Sci.* USA 81:6851-6855 (1985), which are hereby incorporated by reference. CDR grafting is described, for example, in U.S. Pat. Nos. 6,180,370, 5,693, 762, 5,693,761, 5,585,089, and 5,530,101, which are all hereby incorporated by reference for all purposes.

Generally, the goal of making a chimeric antibody is to create a chimera in which the number of amino acids from the intended subject species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089, and 5,693,762; Jones et al., 1986, *Nature* 321:522-25; Riechmann et al., 1988, *Nature* 332:323-27; Verhoeyen et al., 1988, *Science* 239: 1534-36).

Caninized, equinized, and felinized antibodies are known, and are made in like manner as described in connection with humanized antibodies above. See, e.g., U.S. Pat. Nos. 8,076, 456; 7,261,890; 6,881,557; 6,504,013; 5,760,185; and US Patent Application Pub. No. US 2010/0061988.

In one aspect of the invention, the CDRs of the light and heavy chain variable regions of the antibodies provided herein are grafted to framework regions (FRs) from antibodies from the same, or a different, phylogenetic species. For example, the CDRs of the light and heavy chain variable regions of the antibody can be grafted to consensus human, canine, equine, or feline FRs. To create consensus FRs, FRs from several heavy chain or light chain amino acid sequences of the desired species may be aligned to identify a consensus amino acid sequence. In other embodiments, the FRs of the antibody heavy chain or light chain are replaced with the FRs from a different heavy chain or light chain.

In one aspect of the invention, rare amino acids in the FRs of the heavy and light chains of the chimeric protein are not replaced, while the rest of the FR amino acids are replaced. A "rare amino acid" is a specific amino acid that is in a position in which this particular amino acid is not usually found in an FR. Alternatively, the grafted variable regions from the antibody may be used with a constant region that is different from the constant region of. In other embodiments of the invention, the grafted variable regions are part of a single chain Fv antibody.

Nucleic Acids

Nucleic acid molecules that encode a chimeric protein of this invention, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acid molecules can be any length, and/or can comprise one or more additional sequences, for example, regulatory sequences, and/or be part of a larger nucleic acid molecule, for example, a vector. The nucleic acid molecules can be single-stranded or double-stranded and can comprise RNA and/or DNA nucleotides, and artificial variants thereof (e.g., peptide nucleic acids). In some embodiments, the nucleic acid molecules can be present in a composition comprising a pharmaceutically acceptable carrier and can be used in the methods of this invention for therapeutic applications.

In another aspect, the present invention provides vectors comprising a nucleic acid encoding a polypeptide of the invention or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors, Tumor-inducing (Ti) plasmids, ballistic particles carrying recombinant nucleic acids, etc. The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, *Trends Biochem. Sci.* 11:287, Maniatis et al., 1987, *Science* 236:1237, incorporated by reference herein in their entireties), and those that direct inducible expression of a nucleotide sequence in response to particular treatment or condition (e.g., the metallothionein promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, plant, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Preparation of Antibodies

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains. By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci.* USA 85:5879; Ward et al., 1989, *Nature* 334:544, de Graaf et al., 2002, *Methods Mol Biol.* 178:379-87.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, *Methods Mol. Biol.* 178:303-16.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, *BioTechnology*, 10:779.

Conservative modifications may be made to the heavy and light chains described herein (and corresponding modifications to the encoding nucleic acids) to produce a chimeric protein having functional and biochemical characteristics. Methods for achieving such modifications are described herein.

Antibodies and functional fragments thereof according to the invention may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the inventive antibodies or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the chimeric proteins provided herein, or to increase or decrease the affinity of these chimeric proteins for human IgE or for modifying the binding affinity of other chimeric proteins described herein.

Production of Chimeric Proteins

The chimeric proteins of this invention can be prepared by any of a number of conventional techniques. For example, chimeric proteins may be produced by recombinant expression systems, using any technique known in the art. See, for example, *Monoclonal Antibodies, Hybridomas: A New Dimension in Biological Analyses*, Kennet et al. (eds.) Plenum Press, New York (1980): and *Antibodies: A Laboratory Manual*, Harlow and Lane (eds.), Cold Spring Harbor Laboratory Press, Cold Spring Harbor, N.Y. (1988).

Antibodies of the present invention and binding fragments thereof can be produced in hybridoma cell lines or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs of the invention typically comprise a nucleic acid molecule encoding a polypeptide comprising one or more of the following: a heavy chain constant region; a heavy chain variable region; a light chain constant region; a light chain variable region; one or more CDRs of the light or heavy chain of the anti-canine IgE antibody. These nucleic acid sequences are inserted into an appropriate expression vector using standard ligation techniques. In one embodiment, the canine, equine, feline, or human antibody heavy or light chain constant region is appended to the C-terminus of the Canine IgE-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis, or another "tag" for which commercially available antibodies exist, such as FLAG®™, HA (hemagglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, column chromatography, or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding the chimeric protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding a chimeric protein by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region; the CMV promoter; the promoter contained in the 3' long terminal repeat of Rous sarcoma virus; the herpes thymidine kinase promoter; the regulatory sequences of the metallothionein; prokaryotic expression vectors such as the beta-lactamase promoter; or the tac promoter. Also available for use are the following animal transcriptional control regions, which exhibit tissue specificity and have been utilized in transgenic animals: the elastase I gene control region that is active in pancreatic acinar cells; the insulin gene control region that is active in pancreatic beta cells; the mouse mammary tumor virus control region that is active in testicular, breast, lymphoid and mast cells; the albumin gene control region that is active in; the alpha-feto-protein gene control region that is active in liver; the alpha 1-antitrypsin gene control region that is active in the liver; the beta-globin gene control region that is active in myeloid cells; the myelin basic protein gene control region that is active in oligodendrocyte cells in the brain; the myosin light chain-2 gene control region that is active in skeletal muscle; the gonadotropic releasing hormone gene control region that is active in the hypothalamus; and the immunoglobulin gene control region that is active in lymphoid.

An enhancer sequence may be inserted into the vector to increase the transcription in higher eukaryotes of a nucleic acid encoding a chimeric protein of the present invention. Enhancers are cis-acting elements of DNA, usually about 10-300 base pairs in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an antibody of the invention, is co-amplified with the selection gene. As a result, increased quantities of chimeric protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding a chimeric protein is inserted into the proper site of the vector.

The completed vector containing sequences encoding the inventive antibody or immunologically functional fragment thereof and/or other biologic agent of this invention is inserted into a suitable host cell for amplification and/or polypeptide production. The transformation of an expression vector for a chimeric protein into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes a chimeric protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression and produce antibodies with constitutive canine IgE binding properties.

In addition to the foregoing, systems for the production of transgenic plants that produce transgenic antibodies, and from which the antibodies are collected, are known and can also be used to carry out the present invention. Examples of such plants, methods of making such plants, and methods of using such plants for the production and collection of antibodies are described in, for example, U.S. Pat. Nos. 8,071,333; 7,781,647; 7,736,648; 7,247,711; 6,852,319 6,841,659; 6,040,498; and 5,959,177.

Pharmaceutical Compositions and Methods of Use

A. Exemplary Formulations. In certain embodiments, the invention also provides compositions comprising the subject anti-IgE chimeric biologic agent (e.g., chimeric protein) together with one or more of the following: a pharmaceutically acceptable diluent; a carrier; a solubilizer; an emulsifier; a preservative; and/or an adjuvant. Such compositions may contain an effective amount of the chimeric protein. Thus, the use of the chimeric proteins are provided herein in the preparation of a pharmaceutical composition or medicament is also included. Such compositions can be used in the treatment of a variety of diseases such as listed below in the section on exemplary utilities.

Acceptable formulation components for pharmaceutical preparations are nontoxic to recipients at the dosages and concentrations employed. In addition to chimeric proteins provided, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles.

Compositions comprising chimeric proteins of this invention may be prepared for storage by mixing the selected composition having the desired degree of purity with optional formulation agents in the form of a lyophilized cake or an aqueous solution. Further, the chimeric proteins may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

A pharmaceutical composition may involve an effective quantity of a chimeric protein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert materials, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are in the form of sustained- or controlled-delivery formulations. Techniques for formulating a variety of other sustained- or controlled-delivery means, such as liposome carriers, bio-erodible microparticles or porous beads and depot injections can be. Sustained-release preparations may include semi-permeable polymer matrices in the form of shaped articles, e.g. films, or microcapsules, polyesters, hydrogels, polylactides, copolymers of L-glutamic acid and gamma ethyl-L-glutamate, poly (2-hydroxyethyl-methacrylate), ethylene vinyl acetate or poly-D(−)-3-hydroxybutyric acid. Sustained release compositions may also include liposomes, which can be prepared by any of several methods known in the art.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The composition may be formulated for transdermal delivery, optionally with the inclusion of microneedles, microprojectiles, patches, electrodes, adhesives, backings, and/or packaging, or formulations for jet delivery, in accordance with known techniques. See, e.g., U.S. Pat. Nos. 8,043,250; 8,041,421; 8,036,738; 8,025,898; 8,017,146.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing a multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The pharmaceutical compositions of the invention can be delivered parenterally, typically by injection. Injections can be intraocular, intraperitoneal, intraportal, intramuscular, intravenous, intrathecal, intracerebral (intra-parenchymal), intracerebroventricular, intraarterial, intralesional, perilesional or subcutaneous. Eye drops can be used for intraocular administration. In some instances, injections may be localized to the vicinity of a particular bone or bones to which the treatment is targeted. For parenteral administration, the chimeric protein may be administered in a pyrogen-free, parenterally acceptable aqueous solution comprising the chimeric protein in a pharmaceutically acceptable vehicle. A particularly suitable vehicle for parenteral injection is sterile distilled water in which the chimeric proteins are formulated as a sterile, isotonic solution, properly preserved.

Pharmaceutical compositions comprising the subject chimeric proteins may be administered by bolus injection or continuously by infusion, by implantation device, sustained release systems or other means for accomplishing prolonged release. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous release. The preparation may be formulated with agent, such as injectable microspheres, bio-erodible particles, polymeric compounds (such as polylactic acid; polyglycolic acid; or copoly (lactic/glycolic) acid (PLGA), beads or liposomes, that can provide controlled or sustained release of the product which may then be delivered via a depot injection. Formulation with hyaluronic acid has the effect of promoting sustained duration in the circulation.

The subject compositions comprising a chimeric protein may be formulated for inhalation. In these embodiments, a chimeric protein is formulated as a dry powder for inhalation, or chimeric protein inhalation solutions may also be formulated with a propellant for aerosol delivery, such as by nebulization.

Certain pharmaceutical compositions of the invention can be delivered through the digestive tract, such as orally. The subject chimeric proteins that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the chimeric protein. For oral administration, modified amino acids may be used to confer resistance to digestive enzymes. Diluents, flavorings, low melting point waxes, vegetable oils, lubricants, suspending agents, tablet disintegrating agents, and binders may also be employed.

The subject compositions comprising chimeric proteins also may be used ex vivo. In such instances, cells, tissues or organs that have been removed from the patient are exposed to or cultured with the chimeric protein. The cultured cells may then be implanted back into the patient or a different patient or used for other purposes.

In certain embodiments, chimeric proteins can be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

B. Conditions for treatment Subjects to be treated by the methods and compositions of the present invention include any afflicted with a disorder or condition in which reduction of free IgE levels would be beneficial. In particular, disorders or condition in which reduction of IgE is associated with early phase inflammation are of great interest. The subject receiving treatment can be a canine, feline, equine, or human. In particular embodiments, the subject can be a human, dog, cat, or horse.

In some embodiments, the subject is asymptomatic or paucisymptomatic with or without currently receiving an anti-inflammatory agent, an anti-allergy agent, and immunomodulatory agent, or a combination thereof. The term "asymptomatic" refers to a subject who is a carrier for a disease but experiences no symptoms (e.g., a condition might be asymptomatic if it fails to show the noticeable symptoms with which it is usually associated with), whereas the term "paucisymptomatic" refers to a patient which is almost clear of any signs and/or symptoms. Examples of anti-allergy agents and immunomodulatory agents include, but should not be limited to, glucocorticoid, a non-steroidal anti-inflammatory agent, a leukotriene antagonist, a Janus kinase (JAK) inhibitor, an immunoglobulin, an anti-histamine, allergen-specific or non-specific immunotherapy agents, and combinations thereof.

Allergic disorders to be treated with the compositions of the invention comprise allergic inflammation and/or chronic inflammation. Examples of chronic inflammation include, but are not limited to celiac disease, vasculitis, lupus, chronic obstructive pulmonary disease (COPD), irritable bowel disease (IBS), atherosclerosis, arthritis, systemic lupus erythematosus, multiple sclerosis, asthma, chronic peptic ulcer, sinusitis, tuberculosis, rheumatoid arthritis, periodontitis, ulcerative colitis, Crohn's disease, atopic dermatitis (eczema), rosacea, seborrheic dermatitis, and/or psoriasis. Examples of allergic inflammation include, but are not limited to, allergic rhinitis, atopic dermatitis, allergic asthma, allergic conjunctivitis, gastro-intestinal inflammation, urticarial, oral-pharyngeal inflammation, latex allergy, and/or food allergy.

In some embodiments, the allergic disorder to be treated is an inflammatory skin disorder. Examples include, but should not be limited to, atopic dermatitis, eczema, rosacea, seborrheic dermatitis, and/or psoriasis. In some embodiments, the subject to be treated has received and/or is currently receiving treatment, such as cyclosporine, glucorticoids, oclacitinib, lokivetmab, topical moisturizers, baths, or combinations thereof. In some embodiments, the inflammatory skin disorder is atopic dermatitis and the subject being treated is a dog.

C. Dosage. The pharmaceutical compositions that are provided can be administered for prophylactic and/or therapeutic treatments. An "effective amount" refers generally to an amount that is a sufficient, but non-toxic, amount of the active ingredient (i.e., anti-IgE biologic agent, chimeric protein) to achieve the desired effect, which is a reduction or elimination in the severity and/or frequency of symptoms and/or improvement or remediation of damage (e.g., a reduction of flares, delays, relapses, and/or recurrences of lesions in a subject with atopic dermatitis). A "therapeutically effective amount" refers to an amount that is sufficient to remedy a disease state or symptoms, or otherwise prevent, hinder, retard or reverse the progression of a disease or any other undesirable symptom. A "prophylactically effective amount" refers to an amount that is effective to prevent, hinder or retard the onset of a disease state or symptom (e.g., a flare).

In general, toxicity and therapeutic efficacy of the antibody or fragment can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from cell culture and/or animal studies can be used in formulating a range of dosages for subjects for treatment. The dosage of the active ingredient typically lines within a range of circulating concentrations that include the $ED_{50}$ with little or no toxicity. The dosage can vary within this range depending upon the dosage form employed and the route of administration utilized.

The effective amount of a pharmaceutical composition comprising chimeric proteins to be employed therapeutically or prophylactically will depend, for example, upon the therapeutic context and objectives. One skilled in the art will appreciate that the appropriate dosage levels for treatment, according to certain embodiments, will thus vary depending, in part, upon the molecule delivered, the indication for which the chimeric protein is being used, the route of administration, and the size (body weight, body surface or organ size) and/or condition (the age and general health) of the subject. A clinician may titer the dosage and modify the route of administration to obtain the optimal therapeutic effect. Typical dosages range from about 1.0 µg/Kg to about 500 mg/Kg body weight (e.g., from about 1.0 µg/Kg to about 100 µg/Kg, or from about 500 µg/Kg to about 1 mg/Kg, or from about 5 mg/Kg to about 100 mg/Kg subject body weight), or more.

The dosing frequency will depend upon the pharmacokinetic parameters of chimeric protein in the formulation. For example, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Treatment may be continuous over time or intermittent. Further refinement of the appropriate dosage is routinely made by those of ordinary skill in the art and is within the ambit of tasks routinely performed by them. Appropriate dosages may be ascertained through use of appropriate dose-response data.

In some embodiments, the biologic agent is administered in combination with another therapeutic agent. Examples of therapeutic agents include, but are not limited to, anti-infectious agent (e.g., anti-septic agent, anti-biotic agent, anti-fungal agent), an anti-allergy agent, and/or an immunomodulatory agent. The therapeutic agent can be administered simultaneously with the biologic agent and/or can be administered at a different time point. The route of administration of the therapeutic agent can be the same or different as the route of administration for the biologic agent. In some embodiments, the biologic agent is administered in combination with topical moisturizers and/or baths.

To treat a disorder characterized by abnormal or excess expression of IgE, e.g., canine IgE, a composition comprising the anti-IgE biologic agent (e.g., chimeric protein of the invention) may be administered to the subject in an amount and for a time sufficient to induce a sustained improvement in at least one indicator that reflects the severity of the disorder. For example, the biologic agent can be administered about every 1, 2, 3, 4, 5, 6, 7, 8, 9, or 10 or more weeks. In other embodiments, the biologic agent is administered about 1, 2, 3, 4, 5, 6, or 7 or more times a week. An improvement is considered "sustained" if the subject exhibits the improvement on at least two occasions separated by at least one to seven days, or in some instances one to six weeks. The appropriate interval will depend to some extent on what disease condition is being treated; it is within the purview of those skilled in the art to determine the appropriate interval for determining whether the improvement is sustained. For example, improvement is considered sustained if a subject that has atopic dermatitis exhibits a reduction of or delay in flares, relapses and/or recurrences of lesions. The degree of improvement is determined based on signs or symptoms, and may also employ questionnaires that are administered to the subject, such as quality-of-life questionnaires.

Kits

Kits that include a chimeric protein and/or a pharmaceutical composition as described herein are also provided. Some kits include an anti-IgE biologic agent, e.g., chimeric protein, and/or composition in a container (e.g., vial or ampule), and may also include instructions for use of chimeric protein and/or composition in the various methods disclosed above. The chimeric protein and/or composition can be in various forms, including, for instance, as part of a solution or as a solid (e.g., lyophilized powder). The instructions may include a description of how to prepare (e.g., dissolve or resuspend) the chimeric protein in an appropriate fluid and/or how to administer the chimeric protein for the treatment of the diseases described.

The kits may also include various other components, such as buffers, salts, complexing metal ions and other agents described above in the section on pharmaceutical compositions. These components may be included with the chimeric protein or may be in separate containers. The kits may also include other therapeutic agents for administration with the chimeric protein. Examples of such agents include, but are not limited to, agents to treat the disorders or conditions described above.

The following examples are provided solely to illustrate certain aspects of the antibodies, fragments and compositions that are provided herein and thus should not be construed to limit the scope of the claimed invention.

EXAMPLES

Example 1: Allergic Disease Therapy in Dogs, Horses and Cats Using a Chimera of Antibody Specific for Dog IgE and the IgE High Affinity Receptor Alpha Chain The monoclonal antibody (mAb) 5.91 possesses very high affinity for an epitope on canine, equine and feline IgE that is distant from the IgE site bound by the IgE high affinity receptor alpha chain. A single chain variable fragment (scFv) produced using the sequence of the variable region of mAb 5.91 has been demonstrated to bind IgE when injected into dogs, and to reduce circulating IgE as well as IgE-bearing B cells (memory and plasma cells). In order to increase the affinity of a therapeutic anti-IgE peptide and to increase blocking of IgE binding to mast cells and basophils, a chimera of the anti-IgE scFv linked to the recombinant canine IgE high affinity receptor alpha chain (e.g., the recombinant extracellular segment of the canine IgE high affinity receptor alpha chain) has been produced that shows marked increase in binding affinity to IgE as well as the ability to block IgE binding to mast cells. In vitro testing with canine mast cells and with canine lymph node B cells has shown that this chimera blocks IgE binding to mast cells and causes IgE-bearing B cell anergy.

In the present invention, a novel chimeric recombinant protein has been developed to remove IgE from the IgE high affinity receptor (FcεRI) on mast cells and other cells responsible for IgE-dependent allergic reactions. The chimera is composed of (1) a unique single chain variable fragment (scFv) of a monoclonal antibody with specificity for an epitope in the heavy chain of IgE at the constant region 2 (Cε2) linked to (2) the alpha chain of FcεRI. This new chimera also blocks binding of IgE to mast cells and other inflammatory cells bearing FcεRI. Because of these unique properties this chimera will desensitize individuals to allergic reactions resulting from allergen-induced IgE cross-linking of IgE bound to FcεRI on mast cells and other inflammatory cells; and in addition prevent circulating IgE from binding to these cells.

Because the scFv portion of the chimera binds to an epitope on the epsilon chain in the Cε2 domain of IgE that is distant from the binding site for the FcεRI on IgE located in the Cε3 domain, it can bind the chimera to IgE already sensitizing mast cells and potentiates the displacement of the mast cell surface alpha chain portion of the FcεRI by the alpha chain portion of the chimera (FIG. 1).

With regard to the chimera activity in blocking IgE binding to mast cells and other inflammatory cells bearing FcεRI, because of the combined affinities of the scFv and the FcεRI alpha chain portions of this chimera it will far exceed the efficacy of current therapeutic anti-IgE antibodies such as omalizumab in blocking circulating IgE from binding to mast cells and other inflammatory cells.

Figure 4:
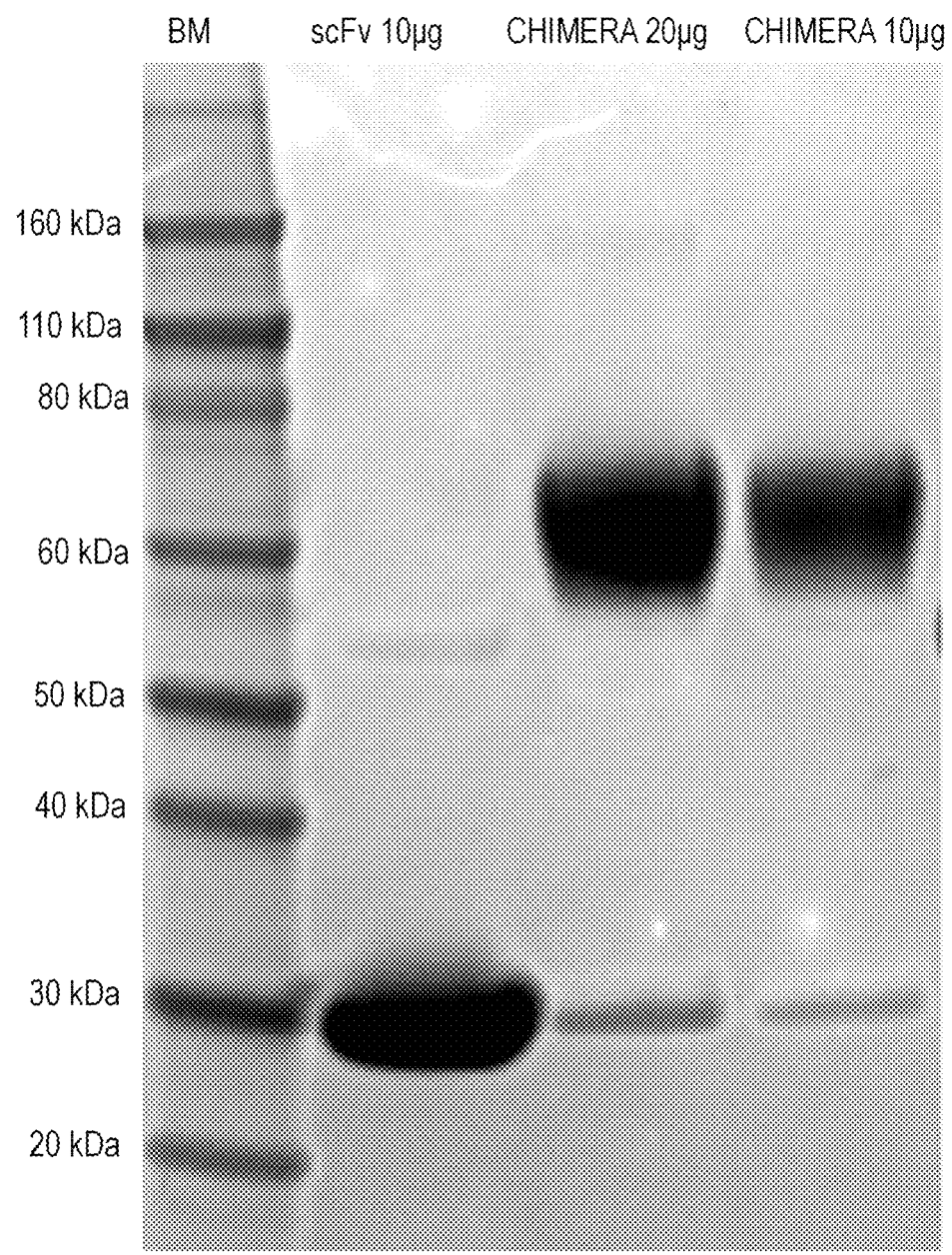
FIG. 4. An image of a portion of a SDS PAGE gel is shown. SDS PAGE under non-reducing conditions of recombinant proteins scFv and chimera of FcεRI×scFv purified by Protein L affinity chromatography from supernatants of HEK 293 cells transfected with plasmids containing the sequence for scFv or FcεRI×scFv, respectively. Molecular weights predicted from amino acid sequences of the recombinant proteins match the molecular weights shown on the SDS PAGE.

Production of scFv and chimera by human embryonic kidney cells, HEK 293, was accomplished by transfection of these cells with plasmids containing sequences for scFv 5.91 (FIG. 2) or for canine FcεRI alpha chain linked to scFv 5.91 (FIG. 3). Protein L affinity purification of scFv 5.91 and the chimera from transfected cell supernatants was done by column chromatography. Purification of the scFv and the chimera of scFv×canine FcεRI alpha chain with expected molecular weight bands was demonstrated by SDS PAGE (FIG. 4).

Figure 5:
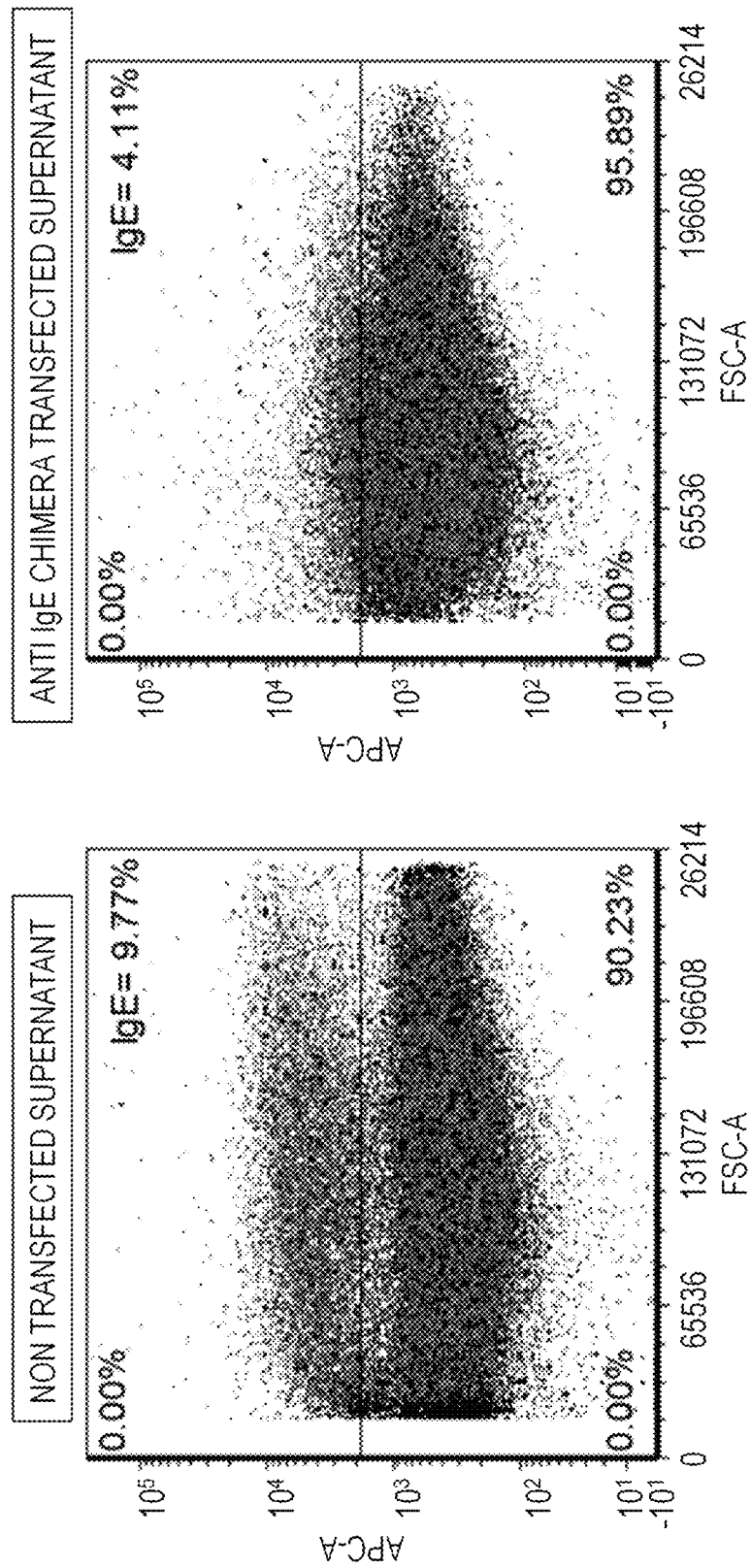
FIG. 5. scFv 5.91×FcεRI alpha chain chimer displacement of IgE from C2 mast cell tumor cells. scFv 5.91×FcεRI alpha chain chimer displacement of IgE from C2 mast cell tumor cells. Supernatant from transfected (right panel) and non-transfected (left panel) Human Embryonic Kidney cells (HEK 293) were incubated with C2 cells for 60 min at room temperature after cells had been activated with canine IgE labeled with fluorescent dye APC for flow cytometric analysis. The reduction in signal from 9.77% to 4.11% cells with label in the upper section is a greater than 50% loss of mast cells carrying IgE.
Figure 6:
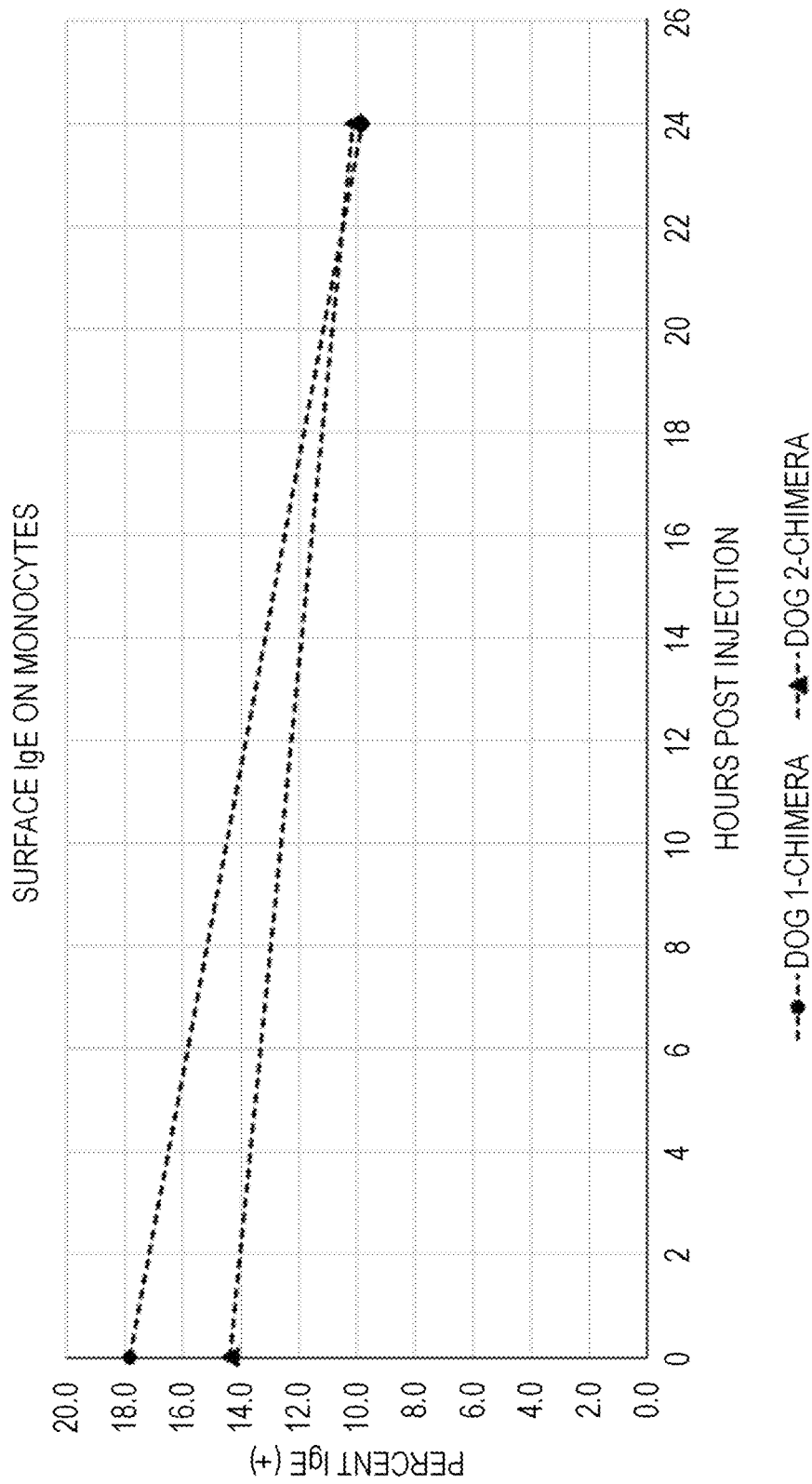
FIG. 6. Reduction of surface bound IgE on circulating monocytes demonstrated by flow cytometry 24 hours after injection of scFv 5.91×FcεRI alpha chain chimera. Dogs 1 and 2 show marked reduction in the percentage of circulating monocytes with detectable surface bound IgE within 24 hours of a single injection of the chimeric protein. Surface bound IgE was measured by fluorescent APC labeled anti-canine IgE monoclonal antibody.

Chimera and scFv titration to end signal on IgE coated ELISA microtiter plates was used to estimate the affinity of each of these recombinant proteins for IgE. Flow cytometry of FcεRI-bearing canine mast cell tumor C2 cells with fluorescent-labeled IgE was used to demonstrate removal of labeled IgE from mast cells by the recombinant protein chimera. Incubation of the mast cells with labeled IgE was followed by incubation with chimera transfected HEK 293 cell supernatant or non-transfected HEK 293 cell supernatant (FIG. 5). FIG. 6 shows in vivo reduction in percentage of inflammatory cells (monocytes) bearing IgE within 24 hours of injection of the chimeric protein.

This application describes a novel chimeric recombinant protein that has not been reported in the literature. The chimera has been designed to bind IgE at two sites such that IgE will be displaced from its binding to mast cells and other inflammatory cells bearing the FcεRI. This property results from the affinity of the chimera exceeding the affinity of the cell surface FcεRI binding IgE. The greater affinity of the chimera for IgE compared to the FcεRI is due to the additive effects of chimera components binding IgE at two different sites. Binding of the scFv portion to an IgE Cε2 domain epitope with an affinity of $2.6 \times 10^{-9}$ M brings the FcεRI alpha chain portion to bind IgE at an enhanced affinity of $1.0 \times 10^{-10}$ M. The resulting affinity of the chimera enables it to displace IgE bound to mast cells and other FcεRI bearing inflammatory cells (FIGS. 1 and 5). Displacement of IgE from mast cells immediately desensitizes these cells, thus preventing inflammatory mediator release even in the presence of allergen exposure.

An unexpected result of the enhanced affinity of the chimera is an observed increased efficacy in reduction of circulating plasma IgE over the scFv-5.91 PEG anti-IgE in two dogs previously shown to be resistant to scFv-5.91 PEG reduction of circulating IgE (FIG. 7). Reduction in circulating IgE is the hallmark measurement for evaluation of efficacy of anti-IgE therapeutic antibodies, and has been shown to be variable in humans treated with omalizumab (Xolair®) with some human subjects showing limited reduction. Thus, the enhanced reduction of circulating IgE by the chimera in two dogs previously shown to be resistant to reduction of IgE by scFv-5.91 PEG is unexpected and significant.

The sustained reduction in circulating IgE after a single injection of the chimera demonstrates that the chimera retains the unexpected properties observed for scFv-5.91 in reducing IgE committed B cells.

The ability of this recombinant chimera to rapidly remove cell-bound IgE and thus quickly desensitize individuals from allergen exposure should result in a rapid relief from clinical signs in allergic individuals. This application will be useful for treatment and prevention of anaphylaxis. The combined activity of immediate relief of manifestation of clinical disease with long-term blocking of IgE sensitization offers a major advantage over current anti-IgE therapy with omalizumab (Xolair®). The desensitization of individuals with the chimera will also greatly reduce the risk of concurrent allergen-specific immunotherapy using multiple applications of increasing concentrations of allergen by oral or injection routes.

Supporting data for safety and enhanced efficacy in reduction of circulating IgE by anti-IgE chimera therapy in two normal dogs is shown here (FIG. 7). These two normal dogs were previously injected one year prior with scFv-5.91 PEG in a trial with four dogs that showed lower efficacy in these two dogs compared with high efficacy in the other two dogs. This variability in anti-IgE therapy among individuals in reduction in circulating IgE responses is well recognized for the current human therapeutic anti-IgE omalizumab (Xolair®). Monitoring plasma IgE levels before and after injection of the anti-IgE scFv-5.91×FcεRI alpha chain chimera shows a marked and sustained reduction of plasma IgE in both dogs.

Monitoring clinical signs for 24 hours after injection with the chimera showed that at therapeutic doses there are no signs of anaphylactic response in either dog (FIG. 7). Anti-IgE scFv-5.91×FcεRI alpha chain chimera (dashed line) or anti-IgE scFv-5.91 PEG (solid line) was injected once subcutaneously at a dose of 2 mg/Kg. Injections with scFv-5.91 PEG were done16 months prior to scFv-5.91×FcεRI alpha chain chimera injections. Dog 2 did not respond to injection with scFv-5.91 PEG and dog 1 showed only a limited response. In contrast, both dogs showed marked and prolonged reduction in circulating IgE after injection with the scFv-5.91×FcεRI alpha chain chimera.

Example 2: Therapeutic Anti-IgE Monoclonal Antibody Single Chain Variable Fragment (scFv) Safety and Immunomodulatory Effects after One Time Injection in Dogs Study dogs. The protocol of this study was approved by the North Carolina State University (NCSU), Institutional Animal Care and Use Committee. Mature, mixed breed dogs were randomly sourced by the Laboratory Animal Resources at North Carolina State University from animal shelters as healthy dogs and maintained with standard vaccination for distemper and rabies, and deworming in indoor runs for at least 6 months before this study. Dogs A and B were neutered females and dogs C and D were intact males. Three dogs were available for 4 months and a fourth dog for 1 month to determine the response to a single subcutaneous injection of pegylated scFv anti-IgE.

Generation of scFv anti-IgE. The heavy and light chain variable regions of a mouse monoclonal antibody (mAb 5.91) with high affinity binding to an epitope in the C2 domain of the epsilon chain of canine IgE were sequenced (Creative Biolabs; Shirley, N.Y., USA) and a scFv DNA sequence created that contained a linkage between the carboxy terminal of the heavy chain and the amino terminal of the light chain using three repeats of glycine 4 serine 1 (GenScript; Piscataway, N.J., USA). This sequence was incorporated into the vector pcDNA3.4TOPO (Thermo Fisher Scientific; Rockford, Ill., USA) for transfection of Expi293F cells by the ExpiFectamine 293 transfection kit (Thermo Fisher Scientific). The scFv secreted by Expi293F cells in culture for 7 days was purified by affinity chromatography with HiTrap protein L agarose beads (GE Healthcare; Pittsburgh, Pa., USA). Affinity pure scFv was pegylated with SAT(PEG)4 (Thermo Fisher Scientific) at lysine primary amine moieties, and concentrated in phosphate buffered saline, pH 8.0 (PBS) to 2 mg/ml using 9K molecular weight cut-off filtration (Thermo Fisher Scientific). All procedures were conducted with endotoxin-free water and buffers with the resulting concentrated pegylated scFv containing less than 0.25 EU/ml of endotoxin.

Gel electrophoresis. Native polyacrylamide gel electrophoresis (PAGE) of scFv and pegylated scFv was conducted under nonreducing conditions using 4-16% polyacrylamide gel (Thermo Fisher Scientific). Native gel electrophoresis samples were not heated to allow detection of noncovalent aggregation of scFv. After running, gels were heated and stained with Coomassie Blue to show protein bands.

scFv binding to IgE in vitro. ELISA was used to compare scFv with the original mAb 5.91 binding to IgE. Microtitre plates (Thermo Fisher Scientific) were coated with a canine monoclonal IgE, generated from mouse 9 dog heterohybridoma cell line 2.39, overnight at pH 9.0 in 0.05 M sodium carbonate buffer, washed in PBS with 0.05% Tween 20 (PBST) and blocked with 1% bovine serum albumin (BSA). After 2 h, plates were washed and dilutions of biotinylated scFv or mAb 5.91 were added and incubated for a further 2 h. Streptavidin-HRP was added after washing followed by a final wash and addition of ABTS. Absorbance at 450 nm was read after 1 h.

Measurement of plasma IgE. ELISA was used to measure IgE in plasma by two different methods to determine total and "free" IgE levels. Both measurements used the same coating of microtitre plates with 10 μg/ml of rabbit IgG anti-IgE that was affinity-purified by canine IgE linked to agarose beads. Blocking with 4% heat inactivated fetal bovine serum (FBS), and washing was as described above. Detection of IgE after incubation with appropriate dilutions of plasma on coated plates was with biotinylated human recombinant FceRT alpha chain to measure "free" canine IgE, and with biotinylated scFv to measure total IgE. Standard curves for concentration were generated for each plate by using serial dilutions of canine monoclonal IgE in place of dog plasma samples.

SPOTS ELISA. The cDNA-derived amino acid sequence for canine IgE heavy chain constant region, or epsilon chain, with accession number AAB72882 was used to produce a matrix sequence of 13 amino acid long peptides offset by three amino acids representing the entire epsilon chain as 139 spots on a cellulose membrane (JPT Peptide Technologies GmbH; Berlin, Germany). Biotinylated mAb 5.91 and scFv were tested for binding to the membrane spots as described by the manufacturer.

Flow cytometry. Five milliliters of whole blood from each dog was collected into EDTA and centrifuged at 400 g for 20 min. Plasma was harvested for analysis of total and free IgE. The packed cells were washed with HBSS-0.5 mM EDTA and cells were suspended back to the original volume. One hundred microliters of washed cells were added to each polystyrene tube for flow cytometry analysis and incubated for 3 min with 3 ml of 4.1 mM lactic acid, pH 3.9 for IgE stripping or with HBSS-0.5 mM EDTA, respectively. Cells were centrifuged and washed once with FBS staining buffer containing 0.1% $NaN_3$ and suspended in 100 μl of staining buffer for labelling with allophycocyanin (APC) conjugated anti-canine IgE antibodies (scFv, mAb 5.91) and anti-CD21

(AbD Serotec; Raleigh, N.C., USA) to detect bound and expressed IgE, and anti-PEG (GenScript; Piscataway, N.J., USA) to detect pegylated scFv. Cells were incubated with labeled antibodies for 1 h at 4° C. with gentle shaking. After incubation, red blood cells were lysed using 1-Step Fix/Lyse Solution (eBioscience; San Diego, Calif., USA). Samples were then analyzed on a Becton Dickinson LSRII system using FCS Express 4 Flow (Denovo Analysis software; Glendale, Calif., USA). Cell populations (granulocytes, monocytes and lymphocytes) were identified by gating on forward (FSC-A) and side angle (SSC-A) light scatter. The total numbers of labelled granulocytes, monocytes and lymphocytes in specific gated regions were recorded and those labelled with anti-IgE were expressed as a percentage of the total gated population.

scFv characterization. scFv isolated from Expi293F cell culture supernatants after 7 days by protein L affinity chromatography and concentrated to 2 mg/ml showed slight opacity that clarified in buffers above pH 9.0. On nondenaturing, native PAGE of scFv, a strong band was visible at the expected molecular weight of the monomer, 27 kDa, as well as a weak band at 54 kDa. In order to eliminate aggregation and minimize dimerization affinity, purified scFv was pegylated at multiple primary amine groups with SAT (PEG)4 (Thermo Fisher Scientific) creating scFv-PEG4-Sacetyl. The pegylated scFv showed minimal dimeric form on native PAGE.

Binding of scFv to canine IgE was compared to the intact IgG2b mAb 5.91 from which it was derived. The endpoint molar concentration for signal on ELISA plates coated with 10 µg/ml of IgE was $2.0 \times 10^{-12}$ M for biotinylated mAb 5.91 and $2.6 \times 10^{-9}$ M for biotinylated scFv.

Biotinylated mAb 5.91 and scFv bound the same IgE epsilon 13mer peptide sequences as demonstrated on SPOTS ELISA. Two adjacent spots were strongly positive, representing a shared amino acid sequence of QKATNIFPYTAPG (SEQ ID NO:1) which is located near the amino terminus of the C2 domain of the IgE epsilon chain.

Clinical response to scFv injection. Subcutaneous injection of pegylated scFv at 2 mg/ml in volumes required to deliver doses of 1 mg/kg to dogs weighing 10-12 kg showed no change in behavior or vital signs in any of the four dogs during continuous observation for 1 h, 60 min intervals for 8 h and at 24 h after injection. Observation measurements included respiratory rate, heart rate, mucous membrane reperfusion and dermal hyperaemia. No defecation was observed within 1 h of injection, nor was vomiting observed during the 24 h after injection. No reaction was observed at the injection site of any of the dogs.

Plasma IgE levels. A sustained, long-term reduction in plasma IgE over 112 days was observed after a single injection of pegylated scFv in three (dogs A-C) of the four dogs. The most notable differences in IgE values seen in comparing the two different detection protocols for each dog were during the first 28 days, after which the sustained reduction pattern for each dog was similar for both protocols. Dog D showed no reduction during the 28 days post-injection (dpi) period it was available for sampling.

Whole blood leucocyte surface IgE. Whole blood leucocytes were gated into granulocyte, monocyte and lymphocyte populations based on FSC-A and SSC-A scatter. The numbers of cells in these populations were within normal values for all dogs and the populations in each dog fluctuated very little over the course of the study. Responses to injection of pegylated scFv did not include changes in gated population numbers. This allowed comparison of percentages of APC-scFv staining cells within gated populations to be reported.

Detection of IgE on blood cells by flow cytometry was carried out with APC-labeled scFv instead of mAb 5.91, because it was shown that APC-scFv positive staining cell populations were more distinctly separated from negative populations for each dog. No pegylated scFv could be detected with anti-PEG antibodies by flow cytometry of blood cells 24 h after injection of pegylated scFv, which eliminated the possibility of pegylated scFv blocking APC-scFv binding to cell surface IgE in flow cytometry measurements.

Because APC-scFv binds IgE that is bound by cell surface FceRI, as would be expected for monocytes and leucocytes, as well as IgE expressed by B lymphocytes committed to IgE production, lactic acid treatment of blood samples, as previously reported, 15 was attempted to distinguish bound and expressed IgE. Comparison of nontreated and lactic acid treated samples showed no consistent difference in APC-scFv positive cell numbers in any of the gated populations, nor any loss of total cell numbers.

The most consistent changes in IgE(+) cell numbers were in the lymphocyte gate where all dogs showed reductions by 14 dpi. Notably, dogs A and B maintained low numbers of IgE(+) lymphocytes, whereas dogs C and D IgE(+) lymphocytes returned quickly to preinjection levels. This decrease in IgE(+) lymphocytes was not associated with any decrease in CD21(+) B cells. Indeed, there appeared to be an increase in CD21(+) lymphocytes following injection of scFv in all four dogs.

The more dramatic responses of dogs A and B in reduction of IgE(+) lymphocytes compared to dogs C and D was also reflected in changes in IgE(+) granulocytes. Dogs A and B showed rapid and sustained loss of APC-scFv staining of cells in the granulocyte gate; however, dog C showed varying changes with both increased and decreased IgE(+) cell numbers, and dog D showed a consistently higher level of IgE(+) granulocytes. APCscFv staining of cells in the monocyte gate did not show any consistent change following scFv injection.

Example 3: Additional Supporting Results from Ongoing Clinical Studies

A proof-of-concept clinical trial was completed to demonstrate the efficacy of the anti-IgE recombinant chimera in preventing allergic flare in highly allergic dogs manifesting with clinical signs of atopic dermatitis. In this trial client-owned dogs under medication with various anti-inflammatory drugs such as corticosteroids, cyclosporine and apoquel were injected with the anti-IgE recombinant chimera at day 0 with 3 mg/kg, day 14 with 2 mg/kg and at day 28 with 2 mg/kg. All anti-inflammatory medications were withdrawn at day 14 and the dogs were monitored for clinical signs of atopic dermatitis daily for 60 days. Three dogs have completed the trial. All three have shown absence of flare without medications for 60 days. All dogs completed the trial and showed absence of flare without medication that varied between 22 and 231 days (these five dogs had a time to flare of 231, 138, 79, 50, and 22 days; median: 79 days).

Figure 8:
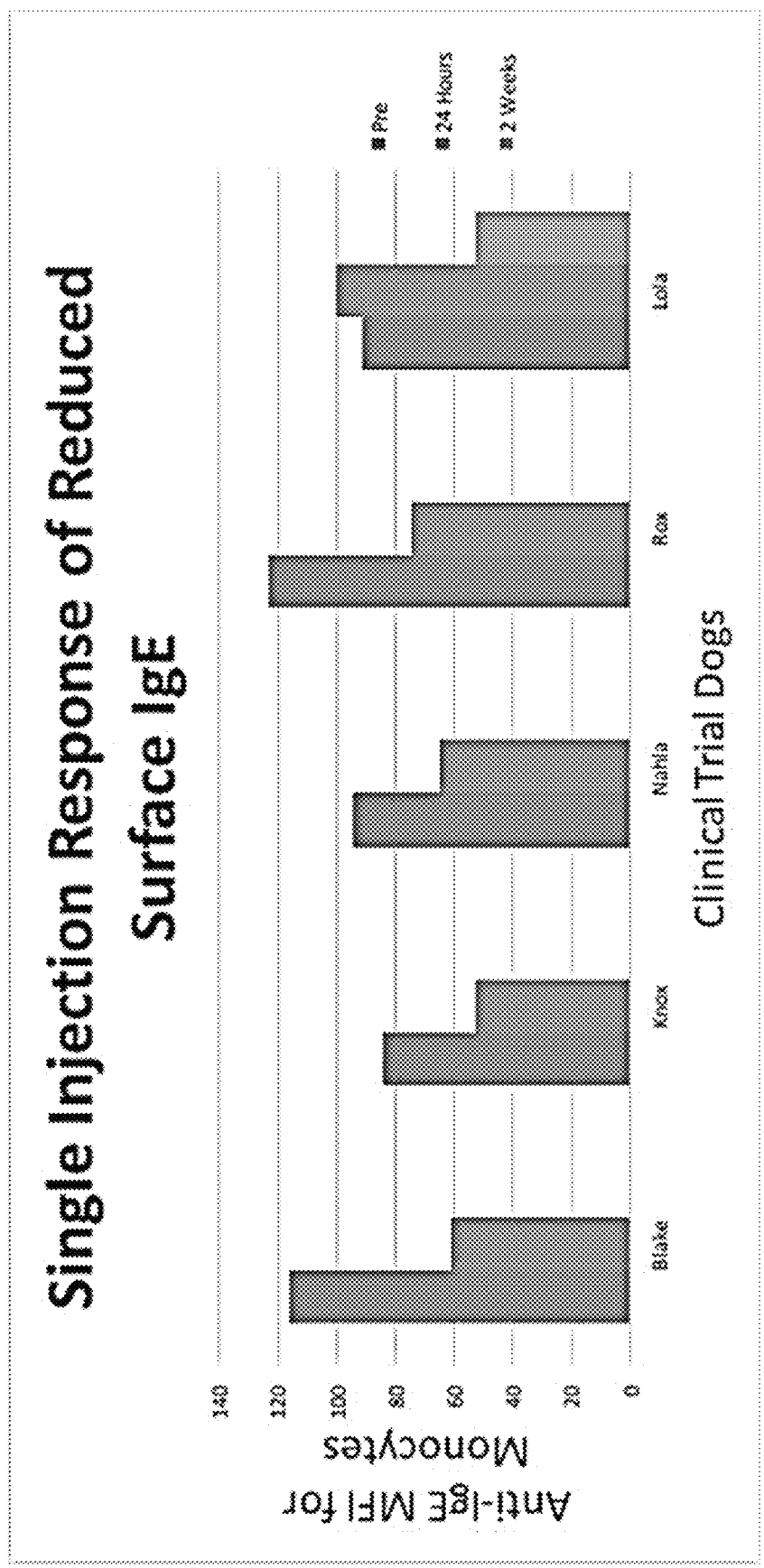
FIG. 8. Rapid response of allergic dogs to a single injection of anti-IgE chimeric antibody. Blood samples were collected at the time of injection, 24 hours post injection, and in one dogs also at 14 days post injection. Blood was incubated with a monoclonal antibody specific for canine IgE labeled with florescent dye for flow cytometric quantitation of circulating monocytes bearing IgE. Mean Florescence Intensity (MFI) of monocyte gated cells was used for quantitation of surface IgE.

Four out of five dogs enrolled in this ongoing study demonstrated a loss of surface bound IgE on circulating monocytes as measured by flow cytometry 24 hours after the initial injection of the anti-IgE chimera shown in FIG. 8. This demonstrates the ability of the chimera to remove IgE bound by high affinity receptors on monocytes in circulation as demonstrated with the mast cell line in vitro (FIG. 5).

Figure 9:
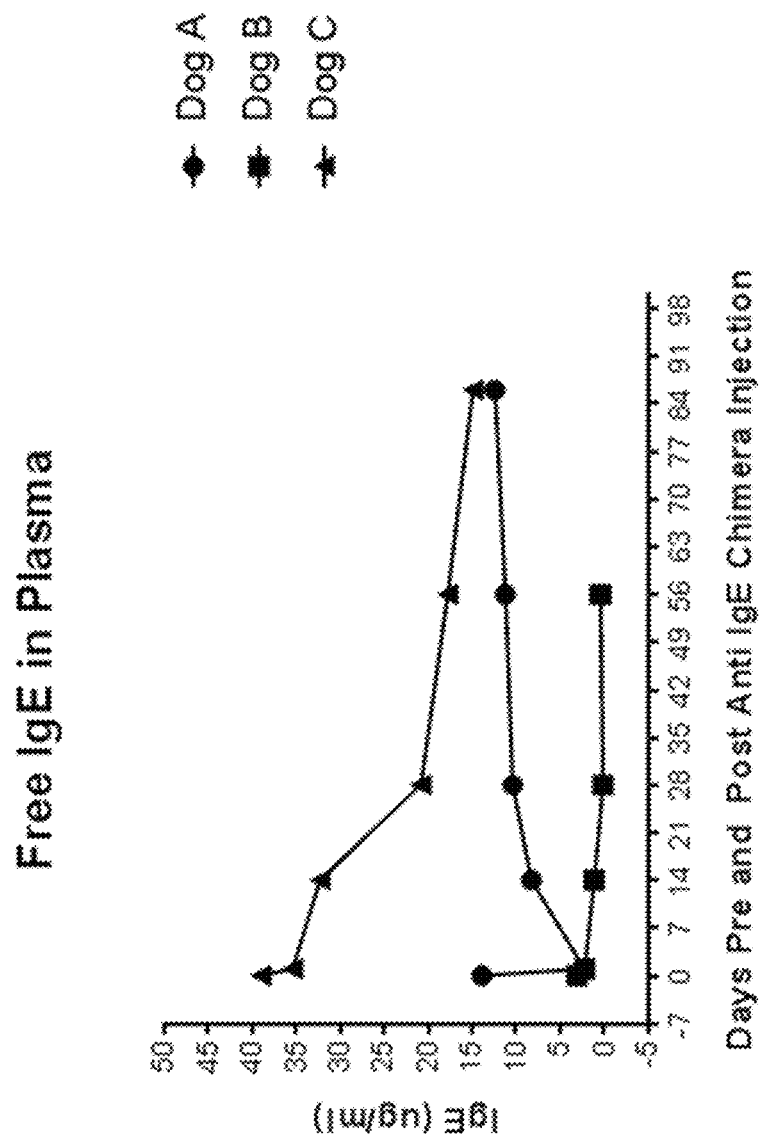
FIG. 9. Total free IgE (not complexed) in plasma of dogs that completed the clinical trial of anti-IgE chimeric recombinant protein. Dogs were injected subcutaneously with the chimeric protein at day 0 with 3 mg/kg, at day 14 with 2 mg/kg and at day 28 with 2 mg/kg. All three dogs showed marked reduction in IgE at 24 hours post injection and sustained low levels for two dogs. All three dogs were protected from allergic flare for at least 60 days after the suspension of corticosteroids and other anti-inflammatory drugs at day 14. Their time to flare after drug removal was as follows: Dog A→231 days (no flare to date), Dog B—138 days, Dog C—70 days.

Measurement of total free (not complexed) plasma IgE in the three dogs that have completed the clinical trial is shown in FIG. 9. Variable long-term reduction of plasma IgE did not correlate with delay in the recurrence of clinical signs suggesting that the anti-IgE recombinant chimera mechanism of action involves complex cellular interaction at the tissue level.

Figure 10:
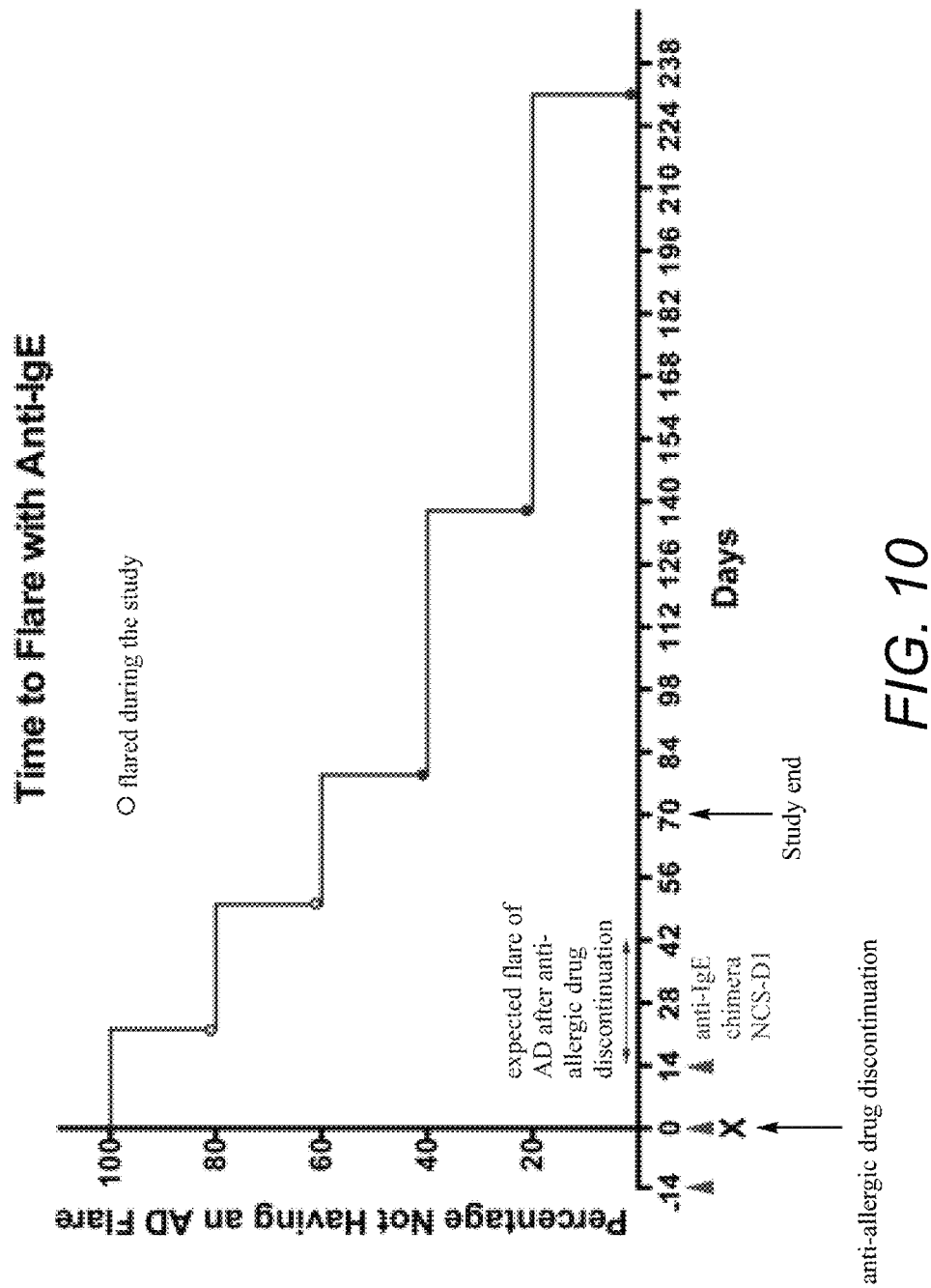
FIG. 10. Results from study showing proactive treatment of canine atopic dermatitis with an anti-IgE chimeric biologic agent (i.e., the anti IgE scFv 5.91×FcεRI alpha chain chimeric protein).

Example 4: Proactive Anti-IgE Therapy in Dogs with Atopic Dermatitis: Proof-of-Concept Despite IgE being thought to be involved in the pathogenesis of human atopic dermatitis (AD), anti-IgE therapy with the monoclonal antibody omalizumab has provided inconsistent benefits and similar data are unavailable in dogs with AD. Our objective was to determine the efficacy of proactive injections of a novel anti-IgE chimera (aIgEc) to delay flares of canine AD in an open 3-month proof-of-concept trial. Five client-owned dogs with chronic, recurrent nonseasonal AD and signs controlled with standard-of-care medications were selected. All dogs received three injections, two weeks apart, of an aIgEc made of a single-chain anti-IgE monoclonal antibody coupled with the extracellular alpha-chain of the high-affinity IgE receptor. Diphenhydramine was given intramuscularly (IM) 30 minutes before each aIgEc injection. After two weeks, all anti-allergic medications were discontinued and dogs were followed until their disease flared and needed treatment. The aIgEc led to a rapid decrease in total IgE within 24 h of the first injection. The median time-to-flare (TTF) of AD after drug discontinuation was 79 days (range 22-231 days). One dog developed a transient focal angioedema after the third injection, a possible treatment-related event. In summary, after only three doses of the aIgEc, the median TTF is more than twice longer than that expected with a placebo, and the values mirror those of dogs receiving continuous twice-weekly proactive topical glucocorticoid therapy (FIG. 10).

Example 5: Proactive Treatment of Canine Atopic Dermatitis with an Anti-IgE Chimeric Biologic Agent In this pilot study, five dogs with nonseasonal atopic dermatitis (AD) having their signs controlled with standard-of-care anti-allergic therapy were treated with a novel caninized (i.e., in the canine sequence) anti-IgE biologic given as three subcutaneous injections, two weeks apart. After the second injection, all previous anti-allergic drugs were discontinued. The primary outcome measure was the time-to-flare (TTF) of AD needing treatment.

In these dogs, the median TTF was 79 days (range: 22-231 days). Three dogs completed the 84-day trial without a flare of their AD, in spite of having only received injections during the first month of treatment. The probability of flare with 3 injections of proactive anti-IgE therapy is depicted in FIG. 10.

Interestingly, this TTF after only 3 injections of the anti-IgE biologic was significantly longer than that of dogs receiving a placebo spray after discontinuation of a glucocorticoid spray (median: 33 days; range: 15-61 days). The TTF of this anti-IgE therapy was not significantly different from that of dogs receiving a mid-potency topical glucocorticoid spray on previously affected areas twice weekly ("proactive topical glucocorticoid therapy"; median: 115 days-range: 31-260 days).

Example 3: Cellular Expression of the High Affinity Receptor for IgE (FcεRI) in Dogs Treated with a Therapeutic Chimera of Anti-IgE Monoclonal Antibody Single Chain Fragment (scFv) Linked to FcεRI Alpha Chain Background of Allergic Diseases Dogs and humans share a high and growing incidence of allergic diseases. Up to 15% of both are afflicted with allergies. In dogs allergies are most commonly seen as atopic dermatitis with skin redness and itching, but rhinitis is also common in dogs. Acute signs of allergic disease, called a flare, occur when the dog or person is exposed to an allergen to which they are sensitized; two examples are pollen and house dust mites. Allergic sensitization is by a very specialized antibody type called Immunoglobulin E or IgE that binds an allergen.

Mechanism of Allergic Reaction

Figure 11:
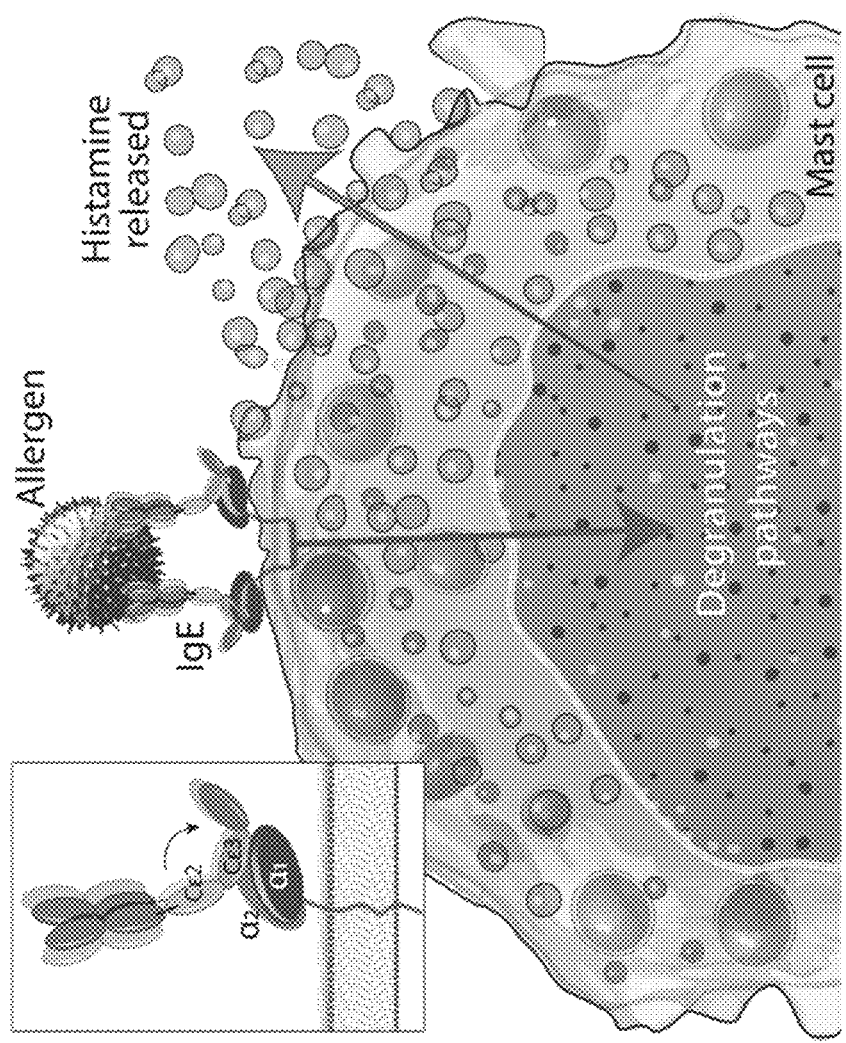
FIG. 11. High affinity receptors for IgE, showing only the alpha chain component that directly binds IgE, are brought together when IgE is cross-linked by binding to allergens. Aggregation of high affinity receptors on the cell surface stimulates degranulation pathways to release histamine and other inflammatory mediators from the cell.

IgE that specifically binds an allergen is tightly bound itself to basophils and mast cells by receptors with high affinity for IgE, FcεRI, (FIG. 11). When two IgE molecules on basophils or mast cells bind to the same allergen they are brought together and stimulate the release of powerful inflammatory mediators such as histamine. Cross-linking of IgE on basophils or mast cells is required for the initiation of an allergic reaction or flare.

Problems with Current Therapies

Figure 12:
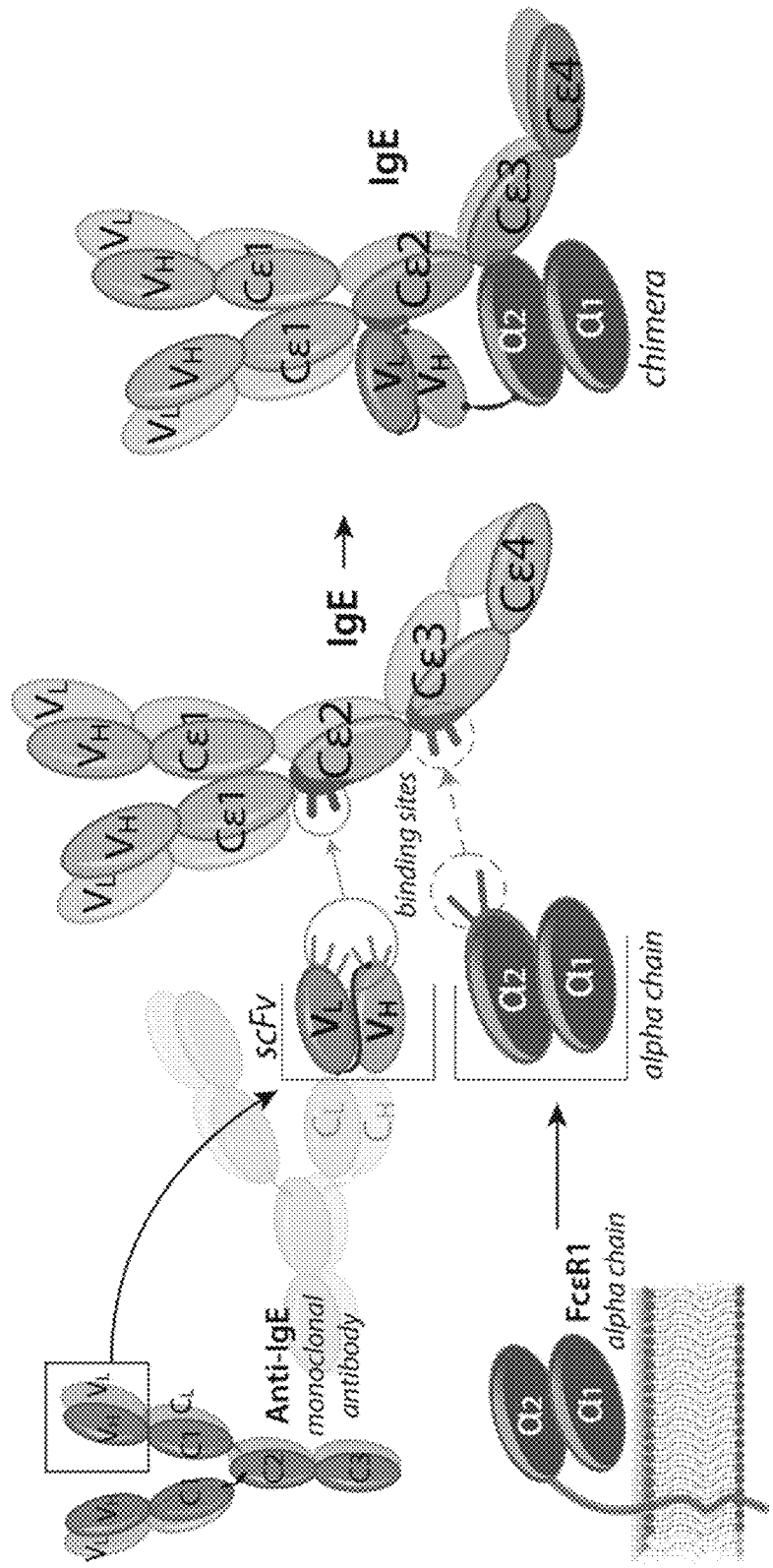
FIG. 12. Chimera construction: domain 1 and domain 2 of the extracellular portion of the FcεRI alpha chain were linked to the anti-IgE single chain variable fragment scFv 5.91 by a poly glycine-serine repeat bridge between the carboxy terminal of alpha chain domain 2 and the amino terminal of the scFv 5.91 variable heavy (VH) region that was in turn linked by a polyglycine-serine repeat to the amino terminal of the scFv 5.91 variable light (VL) region.

Today, the most common drug therapies for allergic diseases block signaling pathways inside inflammatory cells to stop the release of inflammatory mediators or block cells from responding to inflammatory mediators. Unfortunately these drugs, such as corticosteroids, affect many organs and have severe side effects from the long-term use required to control allergic diseases. Mast cell and basophil sensitization with IgE remains intact with current drugs. A novel chimeric recombinant protein has been developed to block IgE binding and to remove IgE from the IgE high affinity receptors (FcεRI) on mast cells and other cells responsible for IgE-dependent allergic reactions. The chimera is composed of the following components: (1) a unique single chain variable fragment (scFv) of a monoclonal antibody with specificity for an epitope in the heavy chain of IgE at the constant region 2 (Cε2) linked to (2) the alpha chain of FcεRI (FIG. 12).

Anti-IgE Therapeutic Chimera of Anti-IgE scFv×FcεRI-Alpha Chain

Chimera Construction

Domain 1 and domain 2 of the extracellular portion of the FcεRI alpha chain were linked to the anti-IgE single chain variable fragment scFv 5.91 by a poly glycine-serine repeat bridge between the carboxy terminal of alpha chain domain 2 and the amino terminal of the scFv 5.91 variable heavy (VH) region that was in turn linked by a polyglycine-serine repeat to the amino terminal of the scFv 5.91 variable light (VL) region.

Figure 13:
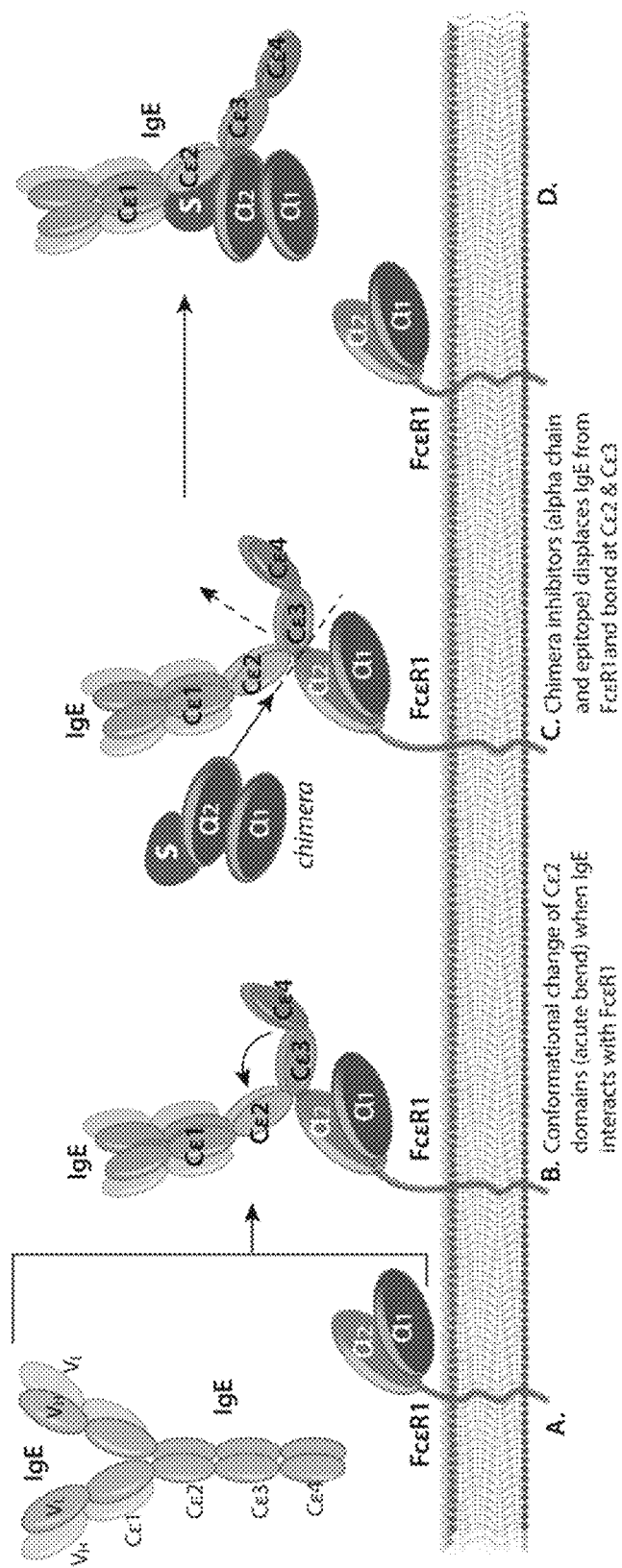
FIG. 13. Mechanism of action. The chimera of scFv 5.91 specific for an epitope in the Cε2 domain of IgE (circle with S) linked to the alpha chain portion of the high affinity receptor for IgE binds free IgE to block activation of mast cells and basophils, as well as displacing IgE already bound to these cell.

Because the scFv portion of the chimera binds to an epitope on the epsilon chain in the Cε2 domain of IgE that is distant from the binding site for the FcεRI on IgE located in the Cε3 domain, the chimera can bind to IgE already sensitizing mast cells and potentiates the displacement of the mast cell surface alpha chain portion of the FcεRI by the alpha chain portion of the chimera (FIGS. 12 and 13).

Preliminary Clinical Trial Shows Protection from Allergic Flare in Allergic Dogs Injected with Anti-IgE Chimera Five dogs diagnosed with atopic dermatitis and requiring daily corticosteroid treatment to prevent itch and erythema were injected subcutaneously with the anti-IgE chimera three times at a 2 week interval at a dosage of 3 mg/kg, 2 mg/kg and 2 mg/kg. Anti-inflammatory medications were stopped 2 weeks after the first anti-IgE injection, at the time of the second injection. Dogs were monitored by their owners on a daily basis for scratching activity and monthly by veterinary dermatology specialists for erythema and lesions. Dogs were monitored until the return of itching, a flare, required corticosteroid treatment. A remarkable duration of protection from flare was observed in two dogs of 124 and 216 days, respectively. Another two dogs were protected for 56 and 48 days. One dog flared at 21 days after stopping medication. Variability in response to anti-IgE therapy in humans with omalizumab over the past decade shows efficacy values ranging from 40 to 60% using monthly injections.

Figure 14:
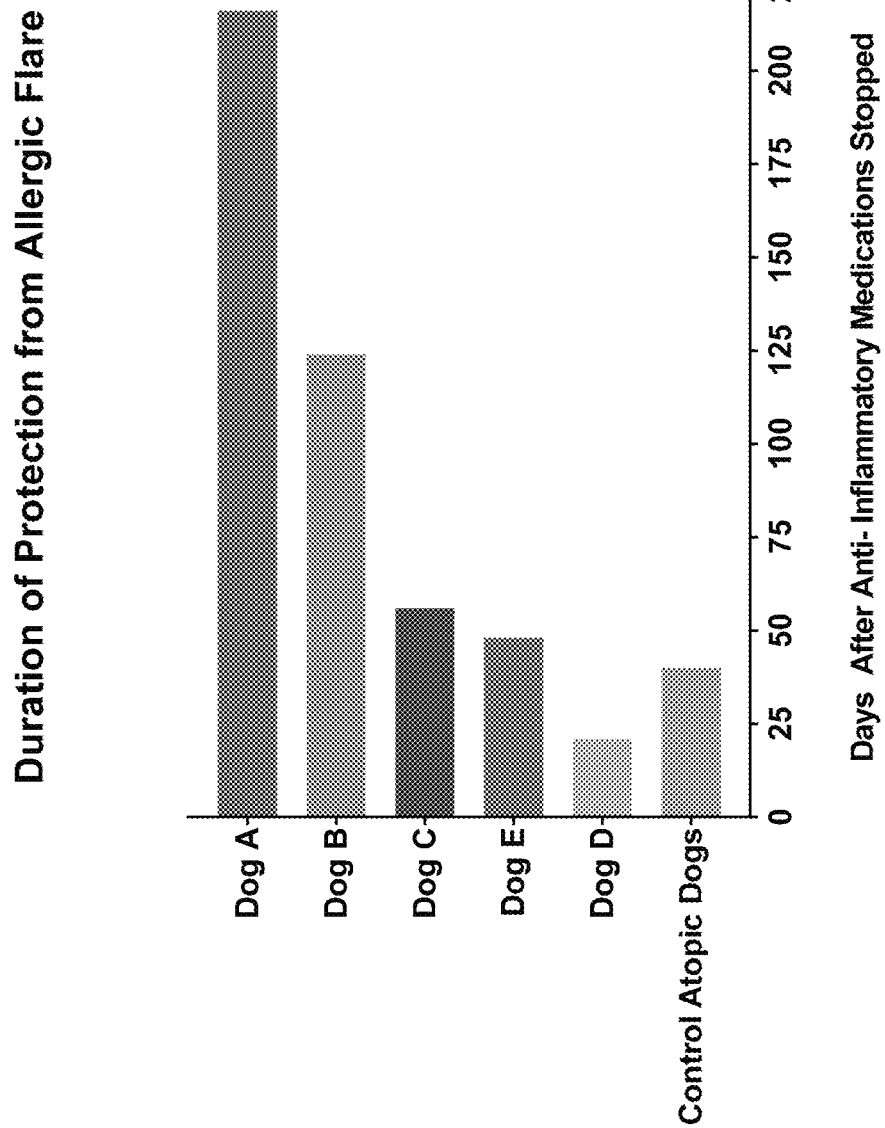
FIG. 14. Protection from allergic flare in dogs with severe atopic dermatitis. Five dogs with long-term histories of atopic dermatitis requiring daily corticosteroid medication were injected subcutaneously with the anti-IgE chimera three times: once with 3 mg/kg, two weeks before medication was stopped, and twice with 2 mg/kg, at the time of withdrawal and two weeks after withdrawal. Ten dogs, represented by the gray bar, with atopic dermatitis used as untreated controls for a separate clinical trial of medication to treat atopic dermatitis showed the range of time to flare without treatment. Improved reduction of circulating IgE by scFv-5.91×FcεRI alpha chain chimera compared to scFv-5.91 PEG after single injection treatment in reduction-resistant dogs.

Five dogs with long-term histories of atopic dermatitis requiring daily corticosteroid medication were injected subcutaneously with the anti-IgE chimera three times: once with 3 mg/kg, two weeks before medication was stopped, and twice with 2 mg/kg, at the time of withdrawal and two weeks after withdrawal. Ten dogs, represented by the gray bar, with atopic dermatitis used as untreated controls for a separate clinical trial of medication to treat atopic dermatitis showed the range of time to flare without treatment (FIG. 14).

Identification of Potential Biomarkers for Clinical Response to Treatment

Figure 15:
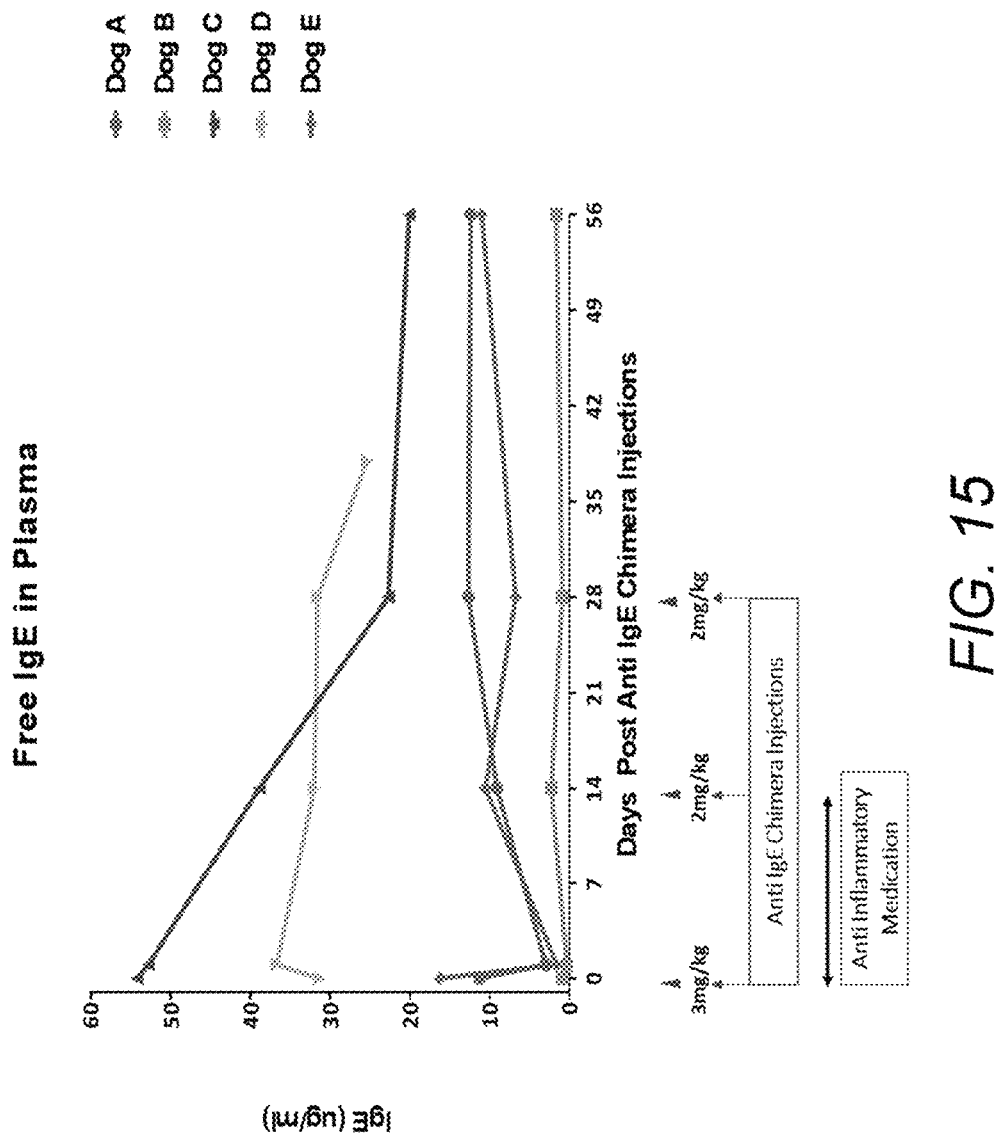
FIG. 15. Measurement of plasma IgE by detection with biotin-labeled human recombinant FcεRI alpha chain on ELISA ("free" IgE). Dogs were bled before anti-IgE chimera injection at day 0, at 24 hours, 14 days, 28 days and 56 days after the first injection. Dog D experienced a flare at 35 days after the first injection and was taken off the study to resume corticosteroid treatment. All dogs received the same dosage of anti-IgE chimera by body weight even though pre-injection free IgE levels ranged from 0.86 to 54.26 µg/ml. Dosage was not calculated based on IgE levels for this clinical trial.

From the observed broad range of clinical responses to this anti-IgE therapy it is clear that the identification of a biomarker that correlates with clinical outcome would be valuable for selective treatment and for dose discovery. During this clinical trial dogs were monitored by serological measurements of IgE (FIG. 15). Measurement of plasma IgE is used during treatment of humans with anti-IgE omalizumab. The involvement of FcεRI alpha chain in many aspects of IgE function indicated including it in this search for a useful biomarker.

Figure 16:
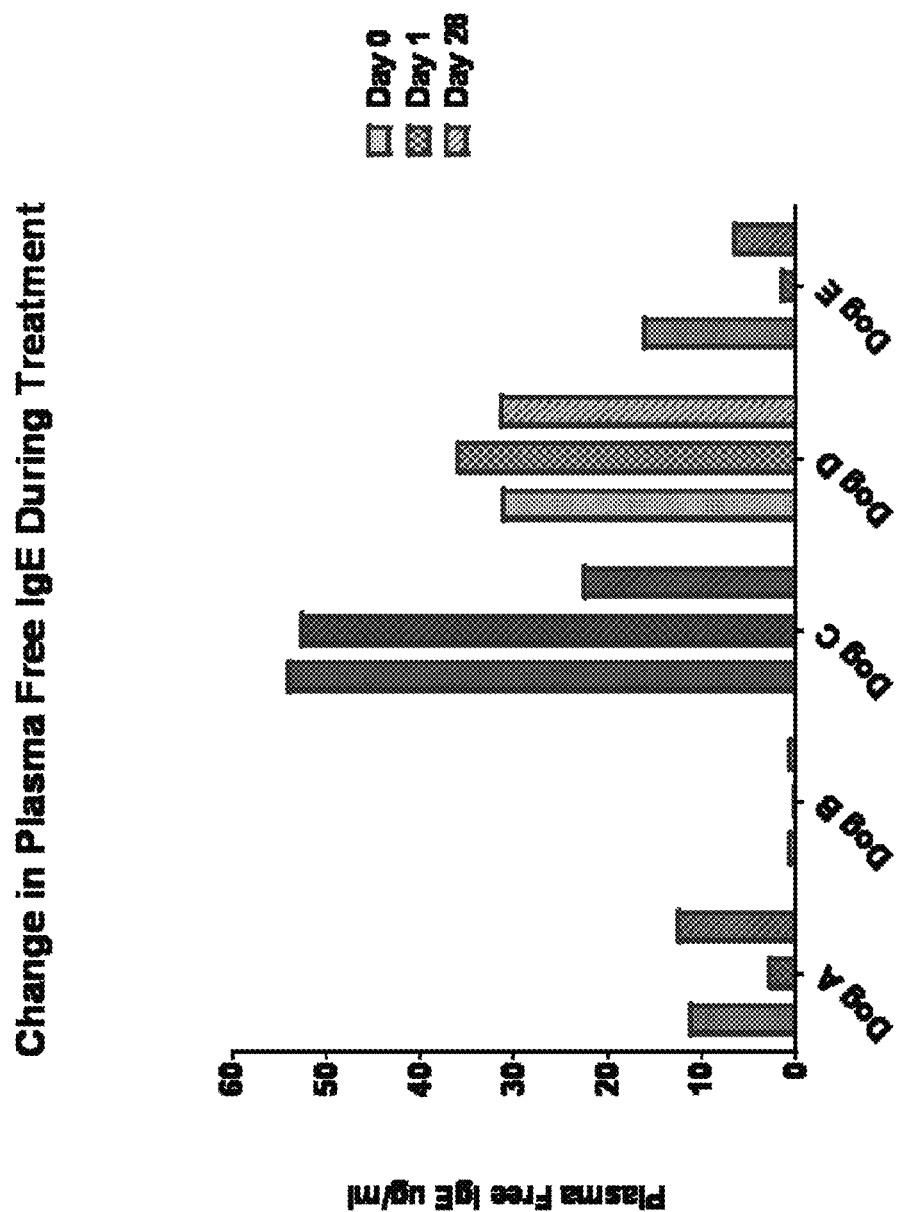
FIG. 16. Values of free plasma IgE from before anti-IgE chimera injection and following the initial injection by 24 hours and two injections at 28 days. Dog A, with the longest protection from flare, showed a marked but brief reduction in IgE. Dog D, with the shortest protection, showed no reduction in IgE as might be expected, but similar intermediate durations of protection in Dogs C and E were dissimilar in IgE reduction profiles.
Figure 17:
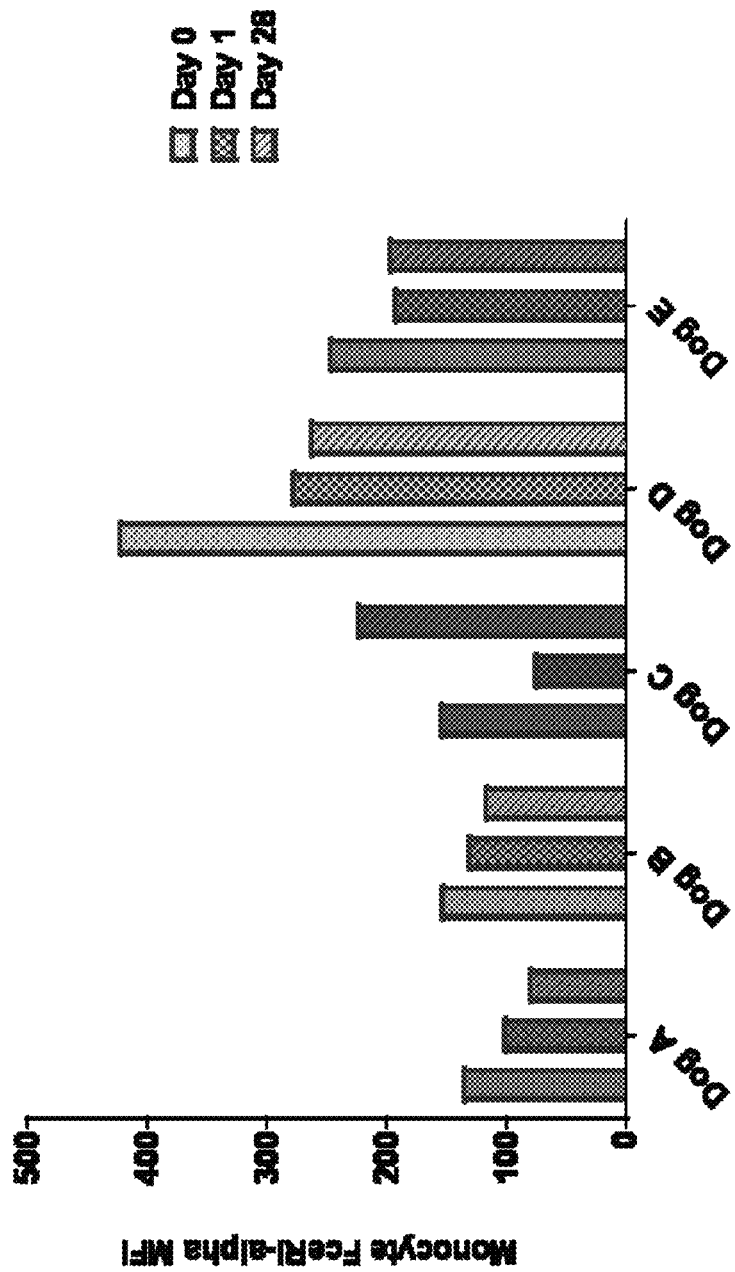
FIG. 17. Values of FcεRI alpha chain expression from before anti-IgE chimera injection and following the initial injection by 24 hours and two injections at 28 days. All five dogs showed reduction of expression of FcεRI alpha chain at 24 hours after the initial injection of chimera, and this reduction was sustained for 28 days with the exception of Dog C. Thus, change in expression did not show a pattern relatable to duration of protection from allergic flare. It was clear that Dog A with the longest protection against return of flare had the lowest pre-injection expression level; whereas, Dog D with the shortest protection duration had the highest pre-injection expression level.

Comparison of Plasma IgE to FcεRI Expression on Monocytes as Biomarkers for Clinical Outcome Values before anti-IgE chimera injection, 24 hours after injection and following two injections (day 28) were considered as absolute values and as change from pre-injection levels. No clear pattern was observed for plasma IgE in change from pre-injection levels to 24 hours or 28 days (FIG. 16). Nor were pre-injection levels of IgE relatable to clinical outcomes (Table 1). No clear pattern was observed for MFI of FcεRI alpha chain expression change from pre-injection levels that related to clinical outcomes (FIG. 17). There was a strong inverse correlation between pre-injection levels of the FcεRI expression and protection from return of allergic flare (Table 1).

CONCLUSIONS

Pre-treatment expression levels of FcεRI alpha chain by monocyte-gated PBC inversely correlated with the duration of protection from return of allergic flare following treatment with an anti-IgE chimeric protein. Sustained reduction in FcεRI alpha chain expression by monocyte-gated cells beyond 28 days was not required for prolonged protection from allergic flare. Plasma levels of free IgE detected by ELISA with labeled FcεRI alpha chain did not correlate with duration of protection from the return of allergic flare.

The foregoing is illustrative of the present invention, and is not to be construed as limiting thereof. The invention is defined by the following claims, with equivalents of the claims to be included therein.

TABLE 1

Biomarkers predictive of response to Anti-IgE therapy

| Dog | Monocyte FcεRI-alpha expression Median Fluorescence Intensity (MFI) | Free IgE in plasma detection by FcεRI-alpha ELISA (μg/ml) | Duration of protection from flare after medication stopped in days |
|---|---|---|---|
| A | 136.71 | 11.31 | 216 |
| B | 154.38 | 0.86 | 124 |
| C | 155.87 | 54.26 | 56 |
| D | 424.85 | 31.34 | 21 |
| E | 248.85 | 16.27 | 48 |
|   | Spearman's Correlation Coefficient = −1 p < 0.0001 | Spearman's Correlation Coefficient = −0.6 p = 0.2848 |  |

That which is claimed is:

1. A chimeric protein comprising:
   a) a single chain variable fragment (scFv), wherein the scFv comprises:
      (i) a light chain (LC) variable region having at the respective complementarity determining regions 1, 2, and 3 (LC-CDR1, LC-CDR2, and LC-CDR3) the amino acid sequences of
         RASGNIHNYL (LC CDR1; SEQ ID NO:2);
         NAKTLAD (LC CDR2; SEQ ID NO:3); and
         FWSTPYT (LC CDR3; SEQ ID NO:4); and
      (ii) a heavy chain (HC) variable region having at the respective complementarity determining regions 1, 2, and 3 (HC-CDR1, HC-CDR2, and HC-CDR3) the amino acid sequences of:
         GYTIH (HC CDR1; SEQ ID NO:5);
         LINPYTGGITYNQNFKGKAT (HC CDR2; SEQ ID NO:6); and
         GPYGNFYAMDY (HC CDR3; SEQ ID NO:7);
   b) a linker peptide, wherein the linker peptide comprises an amino acid sequence of GGGGSGGGGSGGGGS (SEQ ID NO:9) or (GGGS)n (SEQ ID NO:18), wherein n is an integer of 1 to 50; and
   c) an amino acid sequence comprising an IgE high affinity receptor alpha chain of any one of SEQ ID NOs: 10-13.

2. The chimeric protein of claim 1, wherein the scFv binds to human IgE at an epitope within the amino acid sequence EDGQVIVIDVDLSTASTTQ (SEQ ID NO:15).

3. The chimeric protein of claim 1, wherein the scFv binds to equine IgE at an epitope within the amino acid sequence IDGQKVDEQFPTQHGVKQ (SEQ ID NO:16).

4. The chimeric protein of claim 1, wherein the scFv binds to feline IgE at an epitope within the amino acid sequence VDGQKATNIFPYTAPGKQ (SEQ ID NO:17).

5. The chimeric protein of claim 1, wherein the scFv comprises the amino acid sequence:

(SEQ ID NO: 8)
EVQLQQSGPELVKPGASMKISCKASGYSITGYTIHWVKQSHGKNLEW

IGLINPYTGGITYNQNFKGKATLTVDKSSSTAYMELLSLTSEDSAVY

YCSRGPYGNFYAMDYWGQGTSVTVSSGGGGSGGGGSGGGGSDIQMTQ

SPASLSASVGETVTITCRASGNIHNYLAWYQQKQGKSPQLLVYNAKT

LADSVPSRFSGSGSGTQFSLKINSLQPEDFGSYYCQHFWSTPYTFGG

GTKLEIKRA.

6. The chimeric protein of claim 1, wherein the linker peptide comprises the amino acid sequence: GGGGSGGGGSGGGGS (SEQ ID NO:9).

7. A chimeric protein comprising:
   a) a single chain variable fragment (scFv), wherein the scFv comprises:
      (i) a light chain (LC) variable region having at complementarity determining regions (CDRs) thereof at least one, two, or all three of the amino acid sequences of RASGNIHNYL (LC CDR1; SEQ ID NO:2);
         NAKTLAD (LC CDR2; SEQ ID NO:3); and
         FWSTPYT (LC CDR3; SEQ ID NO:4); and/or
      (ii) a heavy chain (HC) variable region having at complementarity determining regions (CDRs) thereof at least one, two, or all three of the amino acid sequences of:
         GYTIH (HC CDR1; SEQ ID NO:5);
         LINPYTGGITYNQNFKGKAT (HC CDR2; SEQ ID NO:6); and
         GPYGNFYAMDY (HC CDR3; SEQ ID NO:7);
   b) a linker peptide; and
   c) an amino acid sequence comprising an IgE high affinity receptor alpha chain, wherein the chimeric protein comprises the amino acid sequence:

(SEQ ID NO: 14)
DTLKPTVSMNPPWNTILKDDSVTLTCTGNNSLEVDSAVWLHNNTTLQE

TTSRLDINKAQIQDSGEYRCRENRSILSDPVYLTVFTEWLILQASANV

VMEGESFLIRCHSWKNLRLTKVTYYKDGIPIRYWYENFNISISNVTTK

NSGNYSCSGQIQQKGYTSKVLNIIVKKEPTKQNKYSGLQGGGGSGGGG

SGGGGSEVQLQQSGPELVKPGASMKISCKASGYSITGYTIHWVKQSHG

KNLEWIGLINPYTGGITYNQNFKGKATLTVDKSSSTAYMELLSLTSED

SAVYYCSRGPYGNFYAMDYWGQGTSVTVSSGGGGSGGGGSGGGGSDIQ

MTQSPASLSASVGETVTITCRASGNIHNYLAWYQQKQGKSPQLLVYNA

KTLADSVPSRFSGSGSGTQFSLKINSLQPEDFGSYYCQHFWSTPYTFG

GGTKLEIKRA.

8. The chimeric protein of claim 1, wherein the scFv is humanized, caninized, felinized, or equinized.

9. The chimeric protein of claim 1, further comprising a water soluble polyalkylene oxide group coupled thereto.

10. The chimeric protein of claim 9, wherein said water soluble polyalkylene oxide group comprises polyethylene glycol.

11. The chimeric protein of claim 1, wherein the single chain variable fragment (scFv) forms an antigen-binding monomer.

12. The chimeric protein of claim 1, which binds to canine IgE at a dissociation constant (Kd) no greater than 500 pM, 100 pM or 10 pM.

13. A composition comprising the chimeric protein of claim 1 in a pharmaceutically acceptable carrier.

14. The chimeric protein of claim 1, wherein the scFv binds to a mammalian IgE at an epitope within the amino acid sequence VDGQKATNIFPYTAPGTK (SEQ ID NO:1) of canine IgE or at an epitope within the corresponding amino acid sequence of a different mammalian species.

15. The chimeric protein of claim 1, wherein the linker peptide is attached to the carboxy terminal of the IgE high affinity receptor alpha chain and is attached to the amino terminal of the scFv.

16. The chimeric protein of claim 1, wherein the linker peptide comprises the amino acid sequence of (GGGS)n (SEQ ID NO:18), wherein n is an integer of 1 to 50.

17. A recombinant nucleic acid molecule encoding the chimeric protein of claim 1.

18. A composition comprising the recombinant nucleic acid molecule of claim 17 in a pharmaceutically acceptable carrier.

19. A host cell containing the recombinant nucleic acid molecule of claim 17.

20. A method of reducing free serum IgE levels in a mammalian subject in need thereof, comprising administering to said subject an effective amount of the chimeric protein of claim 1, thereby reducing free serum IgE levels in the mammalian subject in need thereof.

21. The method of claim 20, wherein said subject is a human, dog, cat, or horse.

22. The method of claim 20, wherein said subject is afflicted with an allergic disorder and said allergic disorder is atopic dermatitis, allergic rhinitis, asthma, allergic conjunctivitis, urticaria, gastro-intestinal inflammation, or oral-pharyngeal inflammation.

23. A method of delaying and/or reducing and/or inhibiting an allergic disorder in a subject in need thereof, comprising administering to the subject an effective amount of the chimeric protein of claim 1, thereby delaying and/or reducing and/or inhibiting the allergic disorder in the subject in need thereof,
wherein the allergic disorder is allergic rhinitis, atopic dermatitis, allergic conjunctivitis, gastro-intestinal inflammation, urticaria, food allergy, celiac disease, vasculitis, chronic obstructive pulmonary disease (COPD), irritable bowel disease (IBS), asthma, sinusitis, atopic dermatitis, rosacea, seborrheic dermatitis, and/or psoriasis.

24. The method of claim 23, wherein the subject is a dog, cat, horse, or human.

25. The method of claim 23, wherein the allergic disorder is allergic rhinitis, atopic dermatitis, allergic conjunctivitis, urticaria, or asthma.

26. The method of claim 23, wherein the subject has received and/or is currently receiving one or more anti-inflammatory agents.

27. The method of claim 20, wherein said subject is afflicted with atopic dermatitis, allergic rhinitis, asthma, allergic conjunctivitis, or urticaria.

28. The method of claim 25, wherein the allergic disorder is asthma and the asthma is allergic asthma.

\* \* \* \* \*

UNITED STATES PATENT AND TRADEMARK OFFICE
CERTIFICATE OF CORRECTION

PATENT NO. : 11,352,443 B2  
APPLICATION NO. : 15/934834  
DATED : June 7, 2022  
INVENTOR(S) : Hammerberg et al.

Page 1 of 1

It is certified that error appears in the above-identified patent and that said Letters Patent is hereby corrected as shown below:

In the Specification

Column 13, Line 2: Please correct "CH domains" to read --$C_H$ domains--

Column 30, Lines 44-45: Please correct "$1.0 \times 10^-_{10}$ M" to read --$1.0 \times 10^{-10}$M--

Column 36, Line 43: Please correct "(C62)" to read --(Cε2)--

In the Claims

Column 51, Line 44, Claim 2:
Please correct "EDGQVIVIDVDLSTASTTQ" to read --EDGQVMDVDLSTASTTQ--

Signed and Sealed this
Eighteenth Day of April, 2023

Katherine Kelly Vidal
*Director of the United States Patent and Trademark Office*

SEQUENCE LISTING

```
<160> NUMBER OF SEQ ID NOS: 18

<210> SEQ ID NO 1
<211> LENGTH: 18
<212> TYPE: PRT
<213> ORGANISM: Artificial
<220> FEATURE:
<223> OTHER INFORMATION: IgE epitope sequence

<400> SEQUENCE: 1

Val Asp Gly Gln Lys Ala Thr Asn Ile Phe Pro Tyr Thr Ala Pro Gly
1               5                   10                  15

Thr Lys

<210> SEQ ID NO 2
<211> LENGTH: 10
<212> TYPE: PRT
<213> ORGANISM: Artificial
<220> FEATURE:
<223> OTHER INFORMATION: light chain complementarity determining region
``` sequence

<400> SEQUENCE: 2

Arg Ala Ser Gly Asn Ile His Asn Tyr Leu
1               5                   10

<210> SEQ ID NO 3
<211> LENGTH: 7
<212> TYPE: PRT
<213> ORGANISM: Artificial
<220> FEATURE:
<223> OTHER INFORMATION: light chain complementarity determining region
      sequence

<400> SEQUENCE: 3

Asn Ala Lys Thr Leu Ala Asp
1               5

<210> SEQ ID NO 4
<211> LENGTH: 7
<212> TYPE: PRT
<213> ORGANISM: Artificial
<220> FEATURE:
<223> OTHER INFORMATION: light chain complementarity determining region
      sequence

<400> SEQUENCE: 4

Phe Trp Ser Thr Pro Tyr Thr
1               5

<210> SEQ ID NO 5
<211> LENGTH: 5
<212> TYPE: PRT
<213> ORGANISM: Artificial
<220> FEATURE:
<223> OTHER INFORMATION: heavy chain complementarity determining region
      sequence

<400> SEQUENCE: 5

Gly Tyr Thr Ile His
1               5

<210> SEQ ID NO 6
<211> LENGTH: 20
<212> TYPE: PRT
<213> ORGANISM: Artificial
<220> FEATURE:
<223> OTHER INFORMATION: heavy chain complementarity determining region
      sequence

<400> SEQUENCE: 6

Leu Ile Asn Pro Tyr Thr Gly Gly Ile Thr Tyr Asn Gln Asn Phe Lys
1               5                   10                  15

Gly Lys Ala Thr
            20

<210> SEQ ID NO 7
<211> LENGTH: 11
<212> TYPE: PRT
<213> ORGANISM: Artificial
<220> FEATURE:
<223> OTHER INFORMATION: heavy chain complementarity determining region
      sequence

<400> SEQUENCE: 7

Gly Pro Tyr Gly Asn Phe Tyr Ala Met Asp Tyr
1               5                   10

```
<210> SEQ ID NO 8
<211> LENGTH: 244
<212> TYPE: PRT
<213> ORGANISM: Artificial
<220> FEATURE:
<223> OTHER INFORMATION: single chain variable fragment sequence

<400> SEQUENCE: 8
```

| Glu | Val | Gln | Leu | Gln | Gln | Ser | Gly | Pro | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |

| Ser | Met | Lys | Ile | Ser | Cys | Lys | Ala | Ser | Gly | Tyr | Ser | Ile | Thr | Gly | Tyr |
|---|---|---|---|---|---|---|---|---|---|---|---|---|---|---|---|
| | | | 20 | | | | | 25 | | | | | 30 | | |

| Thr | Ile | His | Trp | Val | Lys | Gln | Ser | His | Gly | Lys | Asn | Leu | Glu | Trp | Ile |
|---|---|---|---|---|---|---|---|---|---|---|---|---|---|---|---|
| | | 35 | | | | | 40 | | | | | 45 | | | |

| Gly | Leu | Ile | Asn | Pro | Tyr | Thr | Gly | Gly | Ile | Thr | Tyr | Asn | Gln | Asn | Phe |
|---|---|---|---|---|---|---|---|---|---|---|---|---|---|---|---|
| | 50 | | | | | 55 | | | | | 60 | | | | |

| Lys | Gly | Lys | Ala | Thr | Leu | Thr | Val | Asp | Lys | Ser | Ser | Thr | Ala | Tyr |
|---|---|---|---|---|---|---|---|---|---|---|---|---|---|---|
| 65 | | | | | 70 | | | | | 75 | | | | 80 |

| Met | Glu | Leu | Leu | Ser | Leu | Thr | Ser | Glu | Asp | Ser | Ala | Val | Tyr | Tyr | Cys |
|---|---|---|---|---|---|---|---|---|---|---|---|---|---|---|---|
| | | | | 85 | | | | | 90 | | | | | 95 | |

| Ser | Arg | Gly | Pro | Tyr | Gly | Asn | Phe | Tyr | Ala | Met | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Ser | Val | Thr | Val | Ser | Ser | Gly | Gly | Gly | Ser | Gly | Gly | Gly |
|---|---|---|---|---|---|---|---|---|---|---|---|---|---|---|
| | | | 115 | | | | | 120 | | | | | 125 | |

| Gly | Ser | Gly | Gly | Gly | Gly | Ser | Asp | Ile | Gln | Met | Thr | Gln | Ser | Pro | Ala |
|---|---|---|---|---|---|---|---|---|---|---|---|---|---|---|---|
| | 130 | | | | | 135 | | | | | 140 | | | | |

| Ser | Leu | Ser | Ala | Ser | Val | Gly | Glu | Thr | Val | Thr | Ile | Thr | Cys | Arg | Ala |
|---|---|---|---|---|---|---|---|---|---|---|---|---|---|---|---|
| 145 | | | | | 150 | | | | | 155 | | | | | 160 |

| Ser | Gly | Asn | Ile | His | Asn | Tyr | Leu | Ala | Trp | Tyr | Gln | Gln | Lys | Gln | Gly |
|---|---|---|---|---|---|---|---|---|---|---|---|---|---|---|---|
| | | | | 165 | | | | | 170 | | | | | 175 | |

| Lys | Ser | Pro | Gln | Leu | Leu | Val | Tyr | Asn | Ala | Lys | Thr | Leu | Ala | Asp | Ser |
|---|---|---|---|---|---|---|---|---|---|---|---|---|---|---|---|
| | | | 180 | | | | | 185 | | | | | 190 | | |

| Val | Pro | Ser | Arg | Phe | Ser | Gly | Ser | Gly | Ser | Gly | Thr | Gln | Phe | Ser | Leu |
|---|---|---|---|---|---|---|---|---|---|---|---|---|---|---|---|
| | | | 195 | | | | | 200 | | | | | 205 | | |

| Lys | Ile | Asn | Ser | Leu | Gln | Pro | Glu | Asp | Phe | Gly | Ser | Tyr | Tyr | Cys | Gln |
|---|---|---|---|---|---|---|---|---|---|---|---|---|---|---|---|
| | 210 | | | | | 215 | | | | | 220 | | | | |

| His | Phe | Trp | Ser | Thr | Pro | Tyr | Thr | Phe | Gly | Gly | Gly | Thr | Lys | Leu | Glu |
|---|---|---|---|---|---|---|---|---|---|---|---|---|---|---|---|
| 225 | | | | | 230 | | | | | 235 | | | | | 240 |

| Ile | Lys | Arg | Ala |
|---|---|---|---|

```
<210> SEQ ID NO 9
<211> LENGTH: 15
<212> TYPE: PRT
<213> ORGANISM: Artificial
<220> FEATURE:
<223> OTHER INFORMATION: linker peptide sequence

<400> SEQUENCE: 9
```

| Gly | Gly | Gly | Gly | Ser | Gly | Gly | Gly | Ser | Gly | Gly | Gly | Ser |
|---|---|---|---|---|---|---|---|---|---|---|---|---|
| 1 | | | | 5 | | | | 10 | | | | 15 |

```
<210> SEQ ID NO 10
<211> LENGTH: 180
<212> TYPE: PRT
<213> ORGANISM: Homo sapiens

<400> SEQUENCE: 10
```

```
Val Pro Gln Lys Pro Lys Val Ser Leu Asn Pro Pro Trp Asn Arg Ile
 1               5                  10                  15

Phe Lys Gly Glu Asn Val Thr Leu Thr Cys Asn Gly Asn Asn Phe Phe
             20                  25                  30

Glu Val Ser Ser Thr Lys Trp Phe His Asn Gly Ser Leu Ser Glu Glu
         35                  40                  45

Thr Asn Ser Ser Leu Asn Ile Val Asn Ala Lys Phe Glu Asp Ser Gly
     50                  55                  60

Glu Tyr Lys Cys Gln His Gln Gln Val Asn Glu Ser Glu Pro Val Tyr
 65                  70                  75                  80

Leu Glu Val Phe Ser Asp Trp Leu Leu Leu Gln Ala Ser Ala Glu Val
             85                  90                  95

Val Met Glu Gly Gln Pro Leu Phe Leu Arg Cys His Gly Trp Arg Asn
         100                 105                 110

Trp Asp Val Tyr Lys Val Ile Tyr Tyr Lys Asp Gly Glu Ala Leu Lys
     115                 120                 125

Tyr Trp Tyr Glu Asn His Asn Ile Ser Ile Thr Asn Ala Thr Val Glu
             130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                 165                 170                 175

Tyr Trp Leu Gln
             180

<210> SEQ ID NO 11
<211> LENGTH: 183
<212> TYPE: PRT
<213> ORGANISM: Canis lupus familiaris

<400> SEQUENCE: 11

Asp Thr Leu Lys Pro Thr Val Ser Met Asn Pro Pro Trp Asn Thr Ile
 1               5                  10                  15

Leu Lys Asp Asp Ser Val Thr Leu Thr Cys Thr Gly Asn Asn Ser Leu
             20                  25                  30

Glu Val Asp Ser Ala Val Trp Leu His Asn Asn Thr Thr Leu Gln Glu
         35                  40                  45

Thr Thr Ser Arg Leu Asp Ile Asn Lys Ala Gln Ile Gln Asp Ser Gly
     50                  55                  60

Glu Tyr Arg Cys Arg Glu Asn Arg Ser Ile Leu Ser Asp Pro Val Tyr
 65                  70                  75                  80

Leu Thr Val Phe Thr Glu Trp Leu Ile Leu Gln Ala Ser Ala Asn Val
             85                  90                  95

Val Met Glu Gly Glu Ser Phe Leu Ile Arg Cys His Ser Trp Lys Asn
         100                 105                 110

Leu Arg Leu Thr Lys Val Thr Tyr Tyr Lys Asp Gly Ile Pro Ile Arg
     115                 120                 125

Tyr Trp Tyr Glu Asn Phe Asn Ile Ser Ile Ser Asn Val Thr Thr Lys
             130                 135                 140

Asn Ser Gly Asn Tyr Ser Cys Ser Gly Gln Ile Gln Gln Lys Gly Tyr
145                 150                 155                 160

Thr Ser Lys Val Leu Asn Ile Ile Val Lys Lys Glu Pro Thr Lys Gln
                 165                 170                 175

Asn Lys Tyr Ser Gly Leu Gln
             180
```

<210> SEQ ID NO 12
<211> LENGTH: 185
<212> TYPE: PRT
<213> ORGANISM: Felis catus

<400> SEQUENCE: 12

```
Gly Thr Arg Glu Pro Thr Val Ser Leu Asn Pro Pro Trp Thr Thr Ile
1               5                   10                  15

Leu Lys Glu Asp Ser Val Thr Leu Thr Cys Lys Glu Asn Asn Ser Leu
            20                  25                  30

Glu Leu Asn Ser Thr Val Trp Phe His Asn Lys Thr Lys Leu Gly Val
        35                  40                  45

Thr Thr Leu Thr Leu Asp Ile Val Lys Ala Gln Ile Arg Asp Ser Gly
    50                  55                  60

Glu Tyr Thr Cys Gln Asn Lys Gly Ser Met Leu Ser Lys Pro Val Ser
65                  70                  75                  80

Leu Lys Val Phe Arg Glu Trp Leu Leu Leu Gln Ala Ser Thr Glu Val
                85                  90                  95

Val Leu Glu Gly Glu Ser Phe Leu Ile Arg Cys His Ser Trp Arg Asn
            100                 105                 110

Leu Asn Val Lys Lys Val Thr Tyr Tyr Arg Asn Gly Lys Phe Leu Gln
        115                 120                 125

Phe Trp Tyr Asp Asn Tyr Asn Ile Thr Ile Asn Asn Ala Thr Glu Thr
    130                 135                 140

Asp Ser Gly Thr Tyr Tyr Cys Thr Gly Trp Ile Ser Lys Gln Asn His
145                 150                 155                 160

Ile Ser Asn Phe Leu Asn Ile Val Val Arg Lys Asp Ser Pro Pro Glu
                165                 170                 175

His Gln Ser Lys Tyr Tyr Trp Leu Gln
            180                 185
```

<210> SEQ ID NO 13
<211> LENGTH: 185
<212> TYPE: PRT
<213> ORGANISM: Equus caballus

<400> SEQUENCE: 13

```
Ala Ile Arg Lys Ser Thr Val Ser Leu Asn Pro Pro Trp Asn Arg Ile
1               5                   10                  15

Phe Arg Gly Glu Asn Val Thr Leu Thr Cys Asn Lys Asn Lys Pro Leu
            20                  25                  30

Lys Gly Asn Ser Thr Glu Trp Thr Tyr Asn Asn Thr Thr Leu Glu Val
        35                  40                  45

Thr Thr Ser Ser Leu Asn Ile Thr Asn Ala Ser His Arg Ser Ser Gly
    50                  55                  60

Glu Tyr Arg Cys Arg Asn Asn Asp Leu Asn Leu Ser Glu Ala Val His
65                  70                  75                  80

Leu Glu Val Phe Ser Asp Trp Leu Leu Leu Gln Ala Ser Ala Glu Glu
                85                  90                  95

Val Ile Glu Gly Lys Ala Leu Val Leu Arg Cys Arg Gly Trp Lys Asp
            100                 105                 110

Trp Asp Val Phe Lys Val Ile Tyr Tyr Lys Asp Gly Lys Pro Leu Glu
        115                 120                 125

Tyr Trp Tyr Glu Asn Lys Asn Ile Ser Ile Glu Ser Ala Thr Thr Glu
    130                 135                 140
```

Asn Ser Gly Thr Tyr Tyr Cys Glu Gly Ala Phe Asn Phe Lys Arg Thr
145                 150                 155                 160

Ser Glu Arg Tyr Thr Ser Asp Tyr Leu Asn Ile Thr Val Lys Lys Ala
            165                 170                 175

Glu Gln Ser Lys Arg Tyr Trp Leu Gln
        180                 185

<210> SEQ ID NO 14
<211> LENGTH: 442
<212> TYPE: PRT
<213> ORGANISM: Artificial
<220> FEATURE:
<223> OTHER INFORMATION: chimeric protein sequence

<400> SEQUENCE: 14

Asp Thr Leu Lys Pro Thr Val Ser Met Asn Pro Pro Trp Asn Thr Ile
1               5                   10                  15

Leu Lys Asp Asp Ser Val Thr Leu Thr Cys Thr Gly Asn Asn Ser Leu
            20                  25                  30

Glu Val Asp Ser Ala Val Trp Leu His Asn Asn Thr Thr Leu Gln Glu
        35                  40                  45

Thr Thr Ser Arg Leu Asp Ile Asn Lys Ala Gln Ile Gln Asp Ser Gly
    50                  55                  60

Glu Tyr Arg Cys Arg Glu Asn Arg Ser Ile Leu Ser Asp Pro Val Tyr
65                  70                  75                  80

Leu Thr Val Phe Thr Glu Trp Leu Ile Leu Gln Ala Ser Ala Asn Val
                85                  90                  95

Val Met Glu Gly Glu Ser Phe Leu Ile Arg Cys His Ser Trp Lys Asn
            100                 105                 110

Leu Arg Leu Thr Lys Val Thr Tyr Tyr Lys Asp Gly Ile Pro Ile Arg
        115                 120                 125

Tyr Trp Tyr Glu Asn Phe Asn Ile Ser Ile Ser Asn Val Thr Thr Lys
    130                 135                 140

Asn Ser Gly Asn Tyr Ser Cys Ser Gly Gln Ile Gln Gln Lys Gly Tyr
145                 150                 155                 160

Thr Ser Lys Val Leu Asn Ile Ile Val Lys Lys Glu Pro Thr Lys Gln
                165                 170                 175

Asn Lys Tyr Ser Gly Leu Gln Gly Gly Gly Ser Gly Gly Gly
        180                 185                 190

Ser Gly Gly Gly Gly Ser Glu Val Gln Leu Gln Gln Ser Gly Pro Glu
    195                 200                 205

Leu Val Lys Pro Gly Ala Ser Met Lys Ile Ser Cys Lys Ala Ser Gly
210                 215                 220

Tyr Ser Ile Thr Gly Tyr Thr Ile His Trp Val Lys Gln Ser His Gly
225                 230                 235                 240

Lys Asn Leu Glu Trp Ile Gly Leu Ile Asn Pro Tyr Thr Gly Gly Ile
                245                 250                 255

Thr Tyr Asn Gln Asn Phe Lys Gly Lys Ala Thr Leu Thr Val Asp Lys
            260                 265                 270

Ser Ser Ser Thr Ala Tyr Met Glu Leu Leu Ser Leu Thr Ser Glu Asp
        275                 280                 285

Ser Ala Val Tyr Tyr Cys Ser Arg Gly Pro Tyr Gly Asn Phe Tyr Ala
    290                 295                 300

Met Asp Tyr Trp Gly Gln Gly Thr Ser Val Thr Val Ser Ser Gly Gly
305                 310                 315                 320

```
Gly Gly Ser Gly Gly Gly Ser Gly Gly Gly Ser Asp Ile Gln
            325                 330                 335

Met Thr Gln Ser Pro Ala Ser Leu Ser Ala Ser Val Gly Glu Thr Val
            340                 345                 350

Thr Ile Thr Cys Arg Ala Ser Gly Asn Ile His Asn Tyr Leu Ala Trp
        355                 360                 365

Tyr Gln Gln Lys Gln Gly Lys Ser Pro Gln Leu Leu Val Tyr Asn Ala
    370                 375                 380

Lys Thr Leu Ala Asp Ser Val Pro Ser Arg Phe Ser Gly Ser Gly Ser
385                 390                 395                 400

Gly Thr Gln Phe Ser Leu Lys Ile Asn Ser Leu Gln Pro Glu Asp Phe
                405                 410                 415

Gly Ser Tyr Tyr Cys Gln His Phe Trp Ser Thr Pro Tyr Thr Phe Gly
            420                 425                 430

Gly Gly Thr Lys Leu Glu Ile Lys Arg Ala
            435                 440

<210> SEQ ID NO 15
<211> LENGTH: 17
<212> TYPE: PRT
<213> ORGANISM: Artificial
<220> FEATURE:
<223> OTHER INFORMATION: IgE epitope sequence

<400> SEQUENCE: 15

Glu Asp Gly Gln Val Met Asp Val Asp Leu Ser Thr Ala Ser Thr Thr
1               5                   10                  15

Gln

<210> SEQ ID NO 16
<211> LENGTH: 18
<212> TYPE: PRT
<213> ORGANISM: Artificial
<220> FEATURE:
<223> OTHER INFORMATION: IgE epitope sequence

<400> SEQUENCE: 16

Ile Asp Gly Gln Lys Val Asp Glu Gln Phe Pro Thr Gln His Gly Val
1               5                   10                  15

Lys Gln

<210> SEQ ID NO 17
<211> LENGTH: 18
<212> TYPE: PRT
<213> ORGANISM: Artificial
<220> FEATURE:
<223> OTHER INFORMATION: IgE epitope sequence

<400> SEQUENCE: 17

Val Asp Gly Gln Lys Ala Thr Asn Ile Phe Pro Tyr Thr Ala Pro Gly
1               5                   10                  15

Lys Gln
```

```
<210> SEQ ID NO 18
<211> LENGTH: 4
<212> TYPE: PRT
<213> ORGANISM: Artificial
<220> FEATURE:
<223> OTHER INFORMATION: linker peptide

<400> SEQUENCE: 18

Gly Gly Gly Ser
1
```